(12) United States Patent
Panescu

(10) Patent No.: US 8,175,680 B2
(45) Date of Patent: May 8, 2012

(54) SYSTEMS AND METHODS FOR GUIDING CATHETERS USING REGISTERED IMAGES

(75) Inventor: Dorin Panescu, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 857 days.

(21) Appl. No.: 10/322,695

(22) Filed: Dec. 18, 2002

(65) Prior Publication Data

US 2003/0158477 A1 Aug. 21, 2003

Related U.S. Application Data

(63) Continuation-in-part of application No. 10/012,293, filed on Nov. 9, 2001, now abandoned.

(51) Int. Cl.
*A61B 5/05* (2006.01)
(52) U.S. Cl. ...................................... 600/424
(58) Field of Classification Search .................. 600/407, 600/410–411, 417, 424–429, 431, 437, 439; 606/130; 607/122
See application file for complete search history.

(56) References Cited

U.S. PATENT DOCUMENTS

| | | | |
|---|---|---|---|
| 4,697,595 A | 10/1987 | Breyer et al. | |
| 4,706,681 A | 11/1987 | Breyer et al. | |
| 4,951,677 A | 8/1990 | Crowley et al. | |
| 5,000,185 A | 3/1991 | Yock | |
| 5,115,814 A | 5/1992 | Griffith et al. | |
| 5,131,397 A | 7/1992 | Crowley | |
| 5,161,536 A | 11/1992 | Vilkomerson et al. | |
| 5,174,296 A | 12/1992 | Watanabe et al. | |
| 5,211,165 A | 5/1993 | Dumoulin et al. | |
| 5,211,168 A | 5/1993 | Mason et al. | |
| 5,295,486 A * | 3/1994 | Wollschlager et al. | 600/447 |
| 5,314,408 A | 5/1994 | Salmon et al. | |
| 5,345,940 A | 9/1994 | Seward et al. | |

(Continued)

FOREIGN PATENT DOCUMENTS

EP 1 182 619 A2 2/2002

(Continued)

OTHER PUBLICATIONS

PCT Written Opinion of the International Search Authority for PCT/US03/37984, Applicant: Scimed Life System, Inc., Form PCT/ISA/237, dated Apr. 22, 2004 (7 pages).

(Continued)

*Primary Examiner* — Francis Jaworski
(74) *Attorney, Agent, or Firm* — Vista IP Law Group LLP

(57) ABSTRACT

Systems and methods for imaging a body cavity and for guiding a treatment element within a body cavity are provided. A system may include an imaging subsystem having an imaging device and an image processor that gather image data for the body cavity. A mapping subsystem may be provided, including a mapping device and a map processor, to identify target sites within the body cavity, and provide location data for the sites. The system may also include a location processor coupled to a location element on a treatment device to track the location of the location element. The location of a treatment element is determined by reference to the location element. A treatment subsystem including a treatment device having a treatment element and a treatment delivery source may also be provided. A registration subsystem receives and registers data from the other subsystems, and displays the data.

61 Claims, 13 Drawing Sheets

U.S. PATENT DOCUMENTS

| | | | |
|---|---|---|---|
| 5,358,148 A | | 10/1994 | Hanifl et al. |
| 5,383,874 A | | 1/1995 | Jackson et al. |
| 5,391,199 A | | 2/1995 | Ben-Haim |
| 5,398,691 A | * | 3/1995 | Martin et al. ............ 600/463 |
| 5,409,000 A | | 4/1995 | Imran |
| 5,411,025 A | | 5/1995 | Webster, Jr. |
| 5,421,338 A | | 6/1995 | Crowley et al. |
| 5,464,016 A | | 11/1995 | Nicholas et al. |
| 5,485,849 A | | 1/1996 | Panescu et al. |
| 5,494,042 A | | 2/1996 | Panescu et al. |
| 5,515,853 A | | 5/1996 | Smith et al. |
| 5,558,091 A | | 9/1996 | Acker et al. |
| 5,636,634 A | | 6/1997 | Kordis et al. |
| 5,694,945 A | * | 12/1997 | Ben-Haim ............ 600/407 |
| 5,722,403 A | | 3/1998 | McGee et al. |
| 5,724,978 A | | 3/1998 | Tenhoff |
| 5,740,808 A | | 4/1998 | Panescu et al. |
| 5,772,590 A | | 6/1998 | Webster, Jr. |
| 5,782,239 A | | 7/1998 | Webster, Jr. |
| 5,797,849 A | | 8/1998 | Vesely et al. |
| 5,817,022 A | | 10/1998 | Vesely |
| 5,830,145 A | | 11/1998 | Tenhoff |
| 5,833,621 A | | 11/1998 | Panescu et al. |
| 5,840,025 A | | 11/1998 | Ben-Haim |
| 5,840,031 A | * | 11/1998 | Crowley ............ 600/440 |
| 6,019,725 A | | 2/2000 | Vesely et al. |
| 6,027,451 A | | 2/2000 | McGee et al. |
| 6,070,094 A | | 5/2000 | Swanson et al. |
| 6,086,532 A | * | 7/2000 | Panescu et al. ............ 600/437 |
| 6,101,409 A | | 8/2000 | Swanson et al. |
| 6,115,626 A | * | 9/2000 | Whayne et al. ............ 600/427 |
| 6,226,543 B1 | | 5/2001 | Gilboa et al. |
| 6,226,546 B1 | | 5/2001 | Evans |
| 6,228,028 B1 | | 5/2001 | Klein et al. |
| 6,233,476 B1 | | 5/2001 | Strommer et al. |
| 6,233,491 B1 | | 5/2001 | Kordis et al. |
| 6,246,898 B1 | | 6/2001 | Vesely et al. |
| 6,292,681 B1 | | 9/2001 | Moore |
| 6,296,619 B1 | | 10/2001 | Brisken et al. |
| 6,306,096 B1 | | 10/2001 | Seward et al. |
| 6,314,310 B1 | | 11/2001 | Ben-Haim et al. |
| 6,332,089 B1 | | 12/2001 | Acker et al. |
| 6,385,476 B1 | * | 5/2002 | Osadchy et al. ............ 600/407 |
| 6,473,635 B1 | * | 10/2002 | Rasche ............ 600/428 |
| 6,490,474 B1 | | 12/2002 | Willis et al. |
| 6,556,695 B1 | * | 4/2003 | Packer et al. ............ 382/128 |
| 6,685,644 B2 | * | 2/2004 | Seo et al. ............ 600/447 |
| 6,690,963 B2 | * | 2/2004 | Ben-Haim et al. ............ 600/424 |
| 6,711,429 B1 | * | 3/2004 | Gilboa et al. ............ 600/407 |
| 6,719,700 B1 | * | 4/2004 | Willis ............ 600/462 |
| 6,735,465 B2 | * | 5/2004 | Panescu ............ 600/509 |
| 6,895,267 B2 | * | 5/2005 | Panescu et al. ............ 600/424 |
| 7,286,866 B2 | * | 10/2007 | Okerlund et al. ............ 600/407 |
| 7,505,809 B2 | * | 3/2009 | Strommer et al. ............ 600/424 |
| 2003/0078494 A1 | | 4/2003 | Panescu et al. |
| 2003/0093067 A1 | | 5/2003 | Panescu |
| 2003/0158477 A1 | | 8/2003 | Panescu |

FOREIGN PATENT DOCUMENTS

| | | |
|---|---|---|
| WO | WO 99/05971 A1 | 2/1999 |

OTHER PUBLICATIONS

Office Action dated Oct. 23, 2009 in Japanese Patent Application No. 2004-565141, Applicant: Boston Scientific Limited, (7 pages).

Notice of Allowance dated Jun. 17, 2010 in Japanese Patent Application No. 2004-565141, Applicant: Boston Scientific Limited, (3 pages).

Office Action dated Jan. 31, 2011 in Canadian Patent Application No. 2509727, Applicant: Boston Scientific Limited, (2 pages).

Office Action dated Jul. 6, 2011 in European Patent Application No. 03790139.4-2305, Applicant: Boston Scientific Limited, (5 pages).

Office Action dated Sep. 7, 2011 in Canadian Patent Application No. 2509727, Applicant: Boston Scientific Limited, (2 pages).

* cited by examiner

SYSTEMS AND METHODS FOR GUIDING CATHETERS USING REGISTERED IMAGES

RELATED APPLICATIONS

The present application is a continuation-in-part of U.S. Application Ser. No. 10/012,293 filed on Nov. 9, 2001 now abandoned.

FIELD OF THE INVENTION

The present inventions relate generally to systems and methods for guiding and locating diagnostic or therapeutic elements on medical instruments positioned in a body.

BACKGROUND

The use of invasive medical devices, such as catheters and laparoscopes in order to gain access into interior regions or volumes within the body for performing diagnostic and therapeutic procedures is well known. In such procedures, it is important for a physician or technician to be able to precisely position the device, including various functional elements located on the device, within the body in order to make contact with a desired body tissue location.

In order to accurately position the device, it is desirable that the shape or configuration of the particular volume be determined, and registered in a known three-dimensional coordinate system, as well as the location or locations of sites within the volume identified for treatment. Current techniques, however, are incapable of determining and registering the true shape and configuration, as well as the dynamic movement of a volume, or at the least at a resolution high enough to provide a physician a comfortable understanding of the volume. Many current techniques use fluoroscopy to generate an image of the target volume. These devices only provide two-dimensional information about the volume, however, rather than the more preferred three-dimensional information. The result is that physicians using fluoroscopy to obtain an image of the volume within which a medical device is guided must rely partly on their own general knowledge of anatomy to compensate for the two-dimensional image obtained by the fluoroscope. In addition, not only do these device not give the physician a three-dimensional view of the volume, but also do not give an understanding of possible obstacles or movements within the volume itself, such as the opening and closing of valves, atrio-septal defects, atrio-septal defect closure plugs, and the like.

Some technologies are capable of generating and registered three-dimensional images, but these devices are typically incapable of producing a high resolution image of the interior space of the volume, since they operate from outside of the body, or from a location outside of the target volume itself, in the case of transthoracic or transesophageal echography used to image the heart.

Therefore, it would be desirable to provide systems and methods for guiding a medical device that are able to generate higher resolution images of the target volume such that a physician is able to compensate for any obstructions or physical landmarks within the volume itself.

SUMMARY OF THE INVENTION

The present inventions relate generally to systems and methods for guiding and locating diagnostic or therapeutic elements on medical instruments positioned in a body by reconstructing a three-dimensional representation of a subject volume, displaying the representation with or without mapping data, and guiding a device, such as, e.g., a treatment device, by reference to the representation, the mapping data, if available, and the current position of the treatment device within the volume.

In accordance with a first aspect of the present inventions, a method of performing a procedure in a body cavity of a patient, such as a heart chamber, comprises generating three-dimensional image data of the body cavity, generating optional three-dimensional mapping data of the body cavity, registering the image and optional mapping data in a three-dimensional coordinate system, displaying a three-dimensional image of the body cavity based on the registered image data, and displaying an optional three-dimensional map of the body cavity based on the registered mapping data. The three-dimensional map is preferably superimposed over the three-dimensional image. In one procedure, the three-dimensional image data is generated from within the body cavity, and is also generated ultrasonically. Also, the three-dimensional image data preferably comprises a plurality of two-dimensional data slices. In various procedures, the three-dimensional image data or the three-dimensional mapping data, or both, is dynamically displayed. A functional element is moved within the body cavity by registering the movement of the functional element in the coordinate system, and displaying the movement by superimposing the element over the three-dimensional image and optional map. The treatment element is guided by reference to the display, and a target site is treated, such as by ablation, using the treatment element.

The image data can be registered in a variety of ways. For example, a position of a source of the image data within the three-dimensional coordinate system can be determined, and then the image data can be aligned so that the image data source is coincident with the determined position. Or fiducial points within the image data can be generated, positions of the fiducial points within the three-dimensional coordinate system can be determined, and then the image data can be aligned so that the fiducial points are coincident with the determined positions. Or a set of points can be generated, positions of the points within the three-dimensional coordinate system can be determined, and then the image data can be best fit to the set of points. Registration of the image data can even be accomplished at least partially with user intervention.

In a second aspect of the present invention, a method of performing a procedure within a body cavity, such as a heart chamber, comprises internally generating image data, generating mapping data, and registering and displaying the image and mapping data in a three-dimensional coordinate system. In one procedure, both the image and mapping data is three-dimensional. In another procedure, both the image and mapping data is four-dimensional. Preferably, the image data is generated ultrasonically, and comprises a plurality of two-dimensional data slices. A functional element or a treatment element is moved within the body cavity, the movement is registered in the three-dimensional coordinate system, and subsequently displayed. The functional or treatment element is then guided by reference to the display, and treatment is delivered to a target site, such as, by ablating the site.

In a third aspect of the present invention, a method of performing a procedure within a body cavity, such as a heart chamber, comprises internally generating image data and registering the data in a three-dimensional coordinate system. The image data is preferably three-dimensional. Also, the image data is preferably generated over time and dynamically displayed. In one procedure, the image data is generated ultrasonically, and is a plurality of two-dimensional slices. A functional element is moved within the body cavity, and the movement is registered in the coordinate system and displayed.

In a fourth aspect of the present invention, a method of performing a procedure within a body cavity, which may be a heart chamber, comprises introducing an imaging probe with an imaging element and a first location element into the body cavity, generating image data, introducing a mapping probe having one or more mapping elements and a second location element, generating mapping data, determining the locations of the location elements in a three-dimensional coordinate system, registering the image and mapping data in the three-dimensional coordinate system based on the locations of the location elements, and displaying the registered image and mapping data. The imaging element preferably includes an ultrasound transducer. The location elements may include an array of magnetic sensors, or an ultrasound transducer, which may be wired or wireless. Preferably, the first location element is adjacent the imaging element, and the second location element is adjacent the mapping elements. Additionally, a roving probe having a functional element, or a treatment probe having a treatment element, and a third location element is introduced into the body cavity, the location of the third location element in the coordinate system is determined, the location is registered and displayed, and the functional element, or treatment element, is navigated by reference to the display. In one embodiment, the functional element or treatment element is an ablation electrode.

In a fifth aspect of the present invention, a method of performing a procedure within a body cavity, such as a heart chamber, comprises introducing an imaging probe having an imaging element and a first location element in to the body cavity, generating image data, removing the imaging probe, introducing a mapping probe having one or more mapping elements and a second location element into the body cavity, generating mapping data, introducing a roving probe having a functional element and a third location element into the body cavity, determining the locations of the location elements in a three-dimensional coordinate system, registering and displaying the image data, mapping data, and locations of the functional element in the coordinate system based on the locations of the location elements, and navigating the treatment element by reference to the display while the imaging probe is removed from the body cavity. The mapping probe may or may not be removed prior to, or while the roving probe is being deployed or used. The roving probe or mapping probe may be introduced into the body cavity while the imaging probe is removed. The location elements may include an array of magnetic sensors, or an ultrasound transducer, which may be wired or wireless. Preferably, the first location element is adjacent the imaging element, the second location element is adjacent the mapping elements, and the third location element is adjacent the functional element. The imaging element is preferably an ultrasound transducer. In one procedure, the roving probe is a treatment probe and the functional element is a treatment element. Here, the treatment element is guided to a target site by reference to the display, and the target site is treated with the treatment element. In one embodiment, the treatment element is an ablation electrode.

In a sixth aspect of the present invention, a system for treating a target site within a body cavity, which may be a heart chamber, comprises an imaging subsystem having an imaging device with an imaging element and image processing circuitry coupled to the imaging element, a mapping subsystem having a mapping device with one or more mapping elements coupled to map processing circuitry, a treatment delivery subsystem having a treatment device with a treatment element coupled to a treatment delivery source, and a three-dimensional coordinate registration subsystem comprising registration processing circuitry coupled to the image and map processing circuitry, three location elements respectively located on the imaging, mapping, and treatment devices, and location processing circuitry coupled between the location elements and the registration processor. In one embodiment, the three location elements are respectively located adjacent the imaging, mapping, and treatment elements. The registration processing circuitry and the location processing circuitry may be integrated into a single processor. Also, the registration, location, image, and mapping processing circuitry may all be embodied in a single processor. In one embodiment, the location elements comprise three orthogonal arrays of magnetic sensors. Here, the registration subsystem includes an antenna, a magnetic field generator coupled between the antenna and the location processing circuitry, and a magnetic field detector coupled between the location sensors and the location processing circuitry. In another embodiment, the location elements comprise an ultrasound transducer. With this embodiment, the location processing component includes ultrasound transducers, a first ultrasound transceiver coupled between the ultrasound transducers and the location processing circuitry, and a second ultrasound transceiver coupled between the ultrasound transducers and the location processing circuitry.

A display is preferably coupled to the registration subsystem. The imaging element may be an ultrasound transducer, and the imaging device may be an imaging catheter. In one embodiment, the treatment element is an ablation electrode, and the treatment delivery source comprises an ablation energy source.

In a seventh aspect of the present invention, a system for treating a target site within a body cavity, which may be a heart chamber, includes an imaging subsystem having an imaging catheter with an imaging element and image processing circuitry coupled to the imaging element, and a three-dimensional coordinate registration subsystem having registration processing circuitry coupled to the image processing circuitry, a location element on the imaging catheter, and location processing circuitry coupled between the location element and the registration processing circuitry. The system also includes a mapping subsystem having a mapping device with one or more mapping elements coupled to map processing circuitry. The registration processing circuitry is coupled to the map processing circuitry, and also includes another location element on the mapping device coupled to the location processing circuitry. The location element on the imaging catheter is preferably adjacent the imaging element. In one embodiment, the location element includes an orthogonal array of magnetic sensors, and the registration subsystem includes an antenna, a magnetic field generator coupled between the antenna and the location processing circuitry, and a magnetic field detector coupled between the magnetic sensors and the location processing circuitry. In another embodiment, the location element includes an ultrasound transducer, and the registration subsystem includes one or more ultrasound transducers, a first ultrasound transceiver coupled between the one or more ultrasound transducers and the location processing circuitry, and a second ultrasound transceiver coupled between the ultrasound transducer and the location processing circuitry.

In one embodiment, the imaging element comprises an ultrasound transducer, and the imaging catheter is coupled to a pullback device. In one embodiment, the registration processing circuitry and the location processing circuitry are integrated into a single processor. A display is included that is coupled to the registration subsystem.

In an eighth aspect of the present inventions, a system for treating a target site within a body cavity, which may be a heart chamber, includes an imaging subsystem comprising an imaging device configured for generating image data of the body cavity, a probe configured to be moved within the body cavity, and a three-dimensional coordinate registration subsystem configured for registering the image data and the location of the probe within a three-dimensional coordinate system. The probe may be, e.g., a treatment device having a treatment element, in which case, the system may further comprise a treatment delivery subsystem comprising the treatment device and a treatment delivery source coupled to the treatment element. Or the probe may be, e.g., a mapping device configured for generating mapping data, in which case, the system may comprise a mapping subsystem comprising the mapping device, wherein the registration subsystem is further configured for registering the mapping data within the three-dimensional coordinate system. The system may further comprise a display coupled to the registration subsystem. The imaging device can take various forms. For example, the imaging device can be an internal imaging device, e.g., a real time 3-D imaging catheter, or an external imaging device, e.g., a computerized axial tomography device or magnetic resonance imaging device. The registration subsystem can register the image data within the three-dimensional coordinate system in a variety of ways, including using the registration steps described above.

BRIEF DESCRIPTION OF THE DRAWINGS

In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 4b is an isometric view of the treatment delivery subsystem of FIG. 4a;

DETAILED DESCRIPTION

Figure 1:
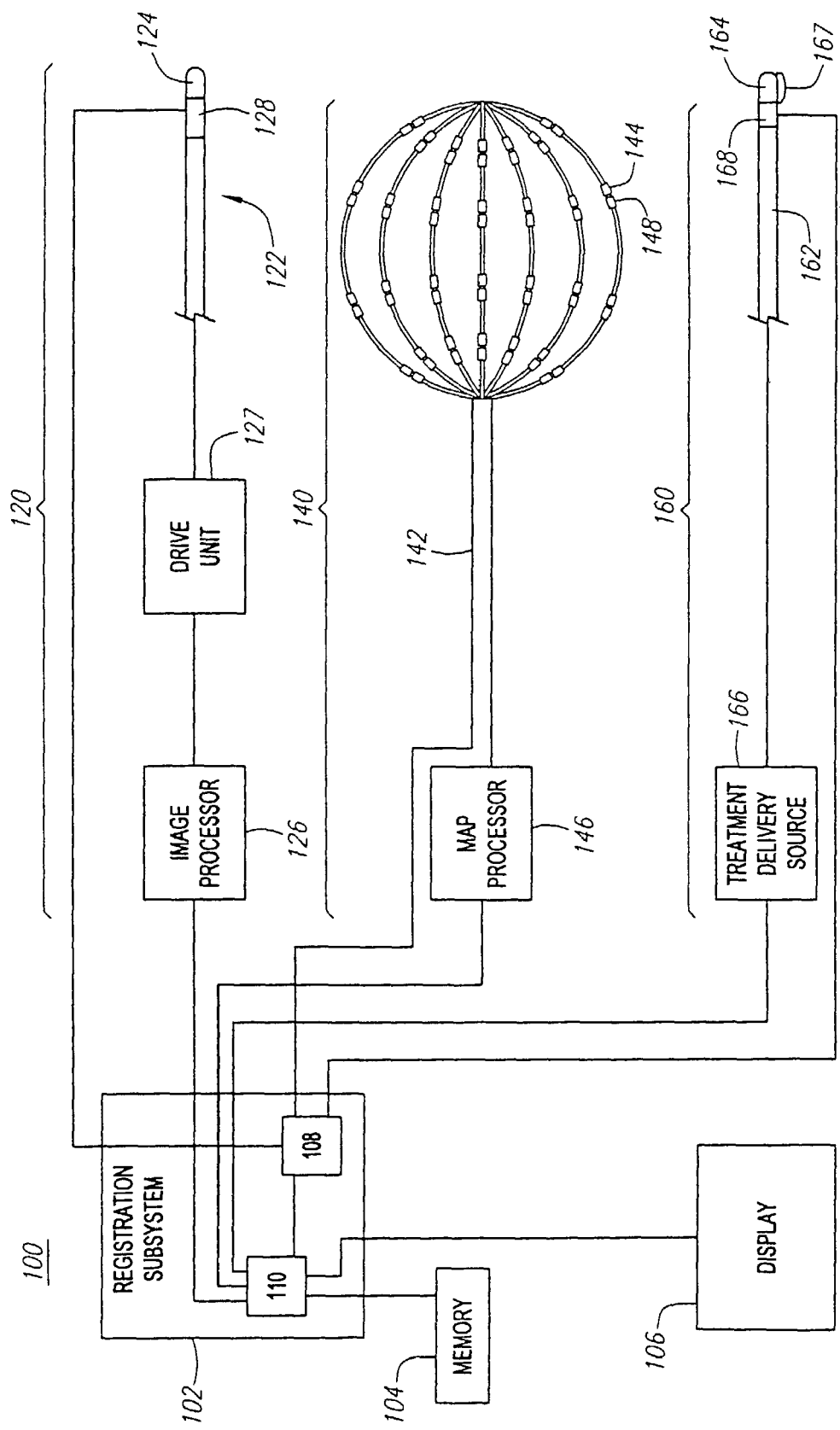
FIG. 1 is a block diagram of one preferred embodiment of a treatment system constructed in accordance with the present inventions.

The present invention provides a system for generating a three-dimensional image of a volume, registering that image in a three-dimensional coordinate system, generating mapping data of the volume, registering the positional data to the three-dimensional coordinate system, and guiding a treatment device to a target site identified by the positional data. The system is particularly suited for reconstructing and mapping a volume within a heart, and for ablating heart tissue. Nevertheless, it should be appreciated that the invention is applicable for use in other applications. For example, the various aspects of the invention have application in procedures for ablating or otherwise treating tissue in the prostate, brain, gall bladder, uterus, esophagus and other regions of the body. Additionally, it should be appreciated that the invention is applicable for use in drug therapy applications where a therapeutic agent is delivered to a targeted tissue region. One preferred embodiment of a treatment system 100, shown in FIG. 1, generally includes a registration subsystem 102, an imaging subsystem 120, a mapping subsystem 140, a treatment delivery subsystem 160, memory 104, and a display 106.

The imaging subsystem 120 includes an imaging device or device 122 with a distally located imaging element 124, and an image processor 126 coupled to the imaging element 124. The embodiment of the imaging subsystem 120 shown in FIG. 1 uses a pullback approach and, therefore, further includes a drive unit 127. As will be described in further detail below, the image processing subsystem 120 gathers data regarding the subject volume that is detected by the imaging device 122, and processed by the image processor 126, and relays that data to the registration subsystem 102, and specifically a registration processor 110. The registration processor 110, with the assistance of a location processor 108 and a location element 128 associated with the imaging element 124, registers the image data in a three-dimensional coordinate system, stores the registered image data in memory 104, and subsequently displays the registered image data on display 106 as a reconstructed three-dimensional image.

The mapping subsystem 140 includes a mapping device 142 with distally located mapping elements 144, and a map processor 146 coupled to the mapping elements 144. Reference herein will be made to a mapping catheter 142 and mapping device 142 interchangeably, but it will be appreciated that the mapping device 142 is not limited to catheters. The mapping subsystem 140 gathers positional data within the subject volume that correspond to specific target sites identified for treatment, using data gathered by the mapping catheter 142 and processed by the map processor 146, and provides the mapping data to the registration processor 110 of the registration subsystem 102. The registration processor 110, with the assistance of the location processor 108 and a location element 148 associated with the mapping elements 144, registers the mapping data in a three-dimensional coordinate system, stores the registered target side data in memory 104, and subsequently displays the registered mapping data, along with the registered image data, on display 106.

The treatment delivery subsystem 160 has a treatment device 162 with a distally located treatment element 164, and a treatment delivery source 166 coupled to the treatment element 164. The treatment device 162, as shown, is a deployable, invasive treatment device 162, such as an ablation catheter, but the treatment device 162 may be any other catheter, surgical device, diagnostic device, measuring instrument, or laparoscopic probe, and is not limited to any particular type of invasive device. The treatment delivery source 166 is an ablation power source when the treatment device 162 is an ablation catheter. In this case, the treatment element 164 is an ablation electrode. The registration processor 110, with the assistance of the location processor 108 and a location element 168 associated with the treatment element 164, registers the location of the treatment element 164 in a three-dimensional coordinate system, and subsequently displays location of the treatment element 164, along with the registered image data and mapping data, on display 106.

In one embodiment, the registration processor 110 and the location processor 108 are incorporated into a single processor. In another embodiment, the registration processor 110, the location processor 108, the image processor 126, and the map processor 146 are all incorporated into a single processor.

The various components of the system 100 will now be discussed in greater detail.

1. Imaging Subsystem

Figure 2:
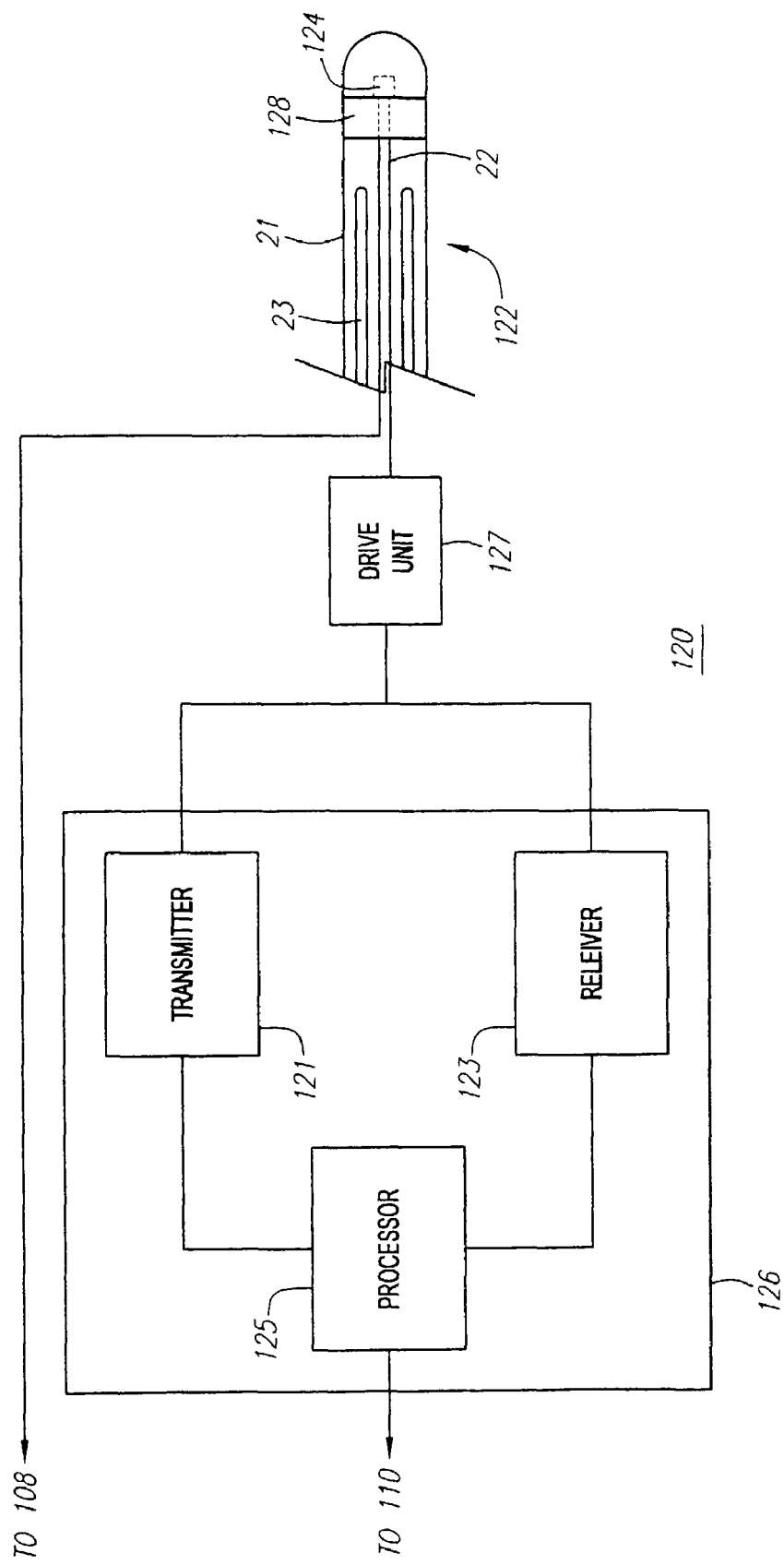
FIG. 2 is a block diagram of an imaging subsystem used in the treatment system of FIG. 1.

The imaging subsystem 120 of the system 100 is used to generate a representation, preferably a three-dimensional representation or image, of the subject volume. One embodiment of the imaging subsystem 120 of the present invention utilizes ultrasound to generate an image of the subject volume. As illustrated in FIG. 2, this embodiment of the imaging subsystem 120 includes the imaging device 122, which is used for gathering images from inside the body. In the illustrated embodiment, the imaging device 122 is an intracardiac device. As illustrated in FIG. 2, the imaging device 122 is a telescoping catheter that generally includes a hollow, outer sheath 21 and a hollow, inner shaft 23. Alternatively, the outer sheath 21 can be a stand-alone element that does not form a part of the imaging catheter 122. A rotatable drive cable 22 extends through the outer sheath 21 and has an imaging element 124 mounted at its distal end. Here, the imaging element 124 is an ultrasonic transducer. For purposes of describing this embodiment of the imaging subsystem, the imaging element 124 will also be referred to as an ultrasonic transducer 124. The transducer 124 preferably includes one or more piezoelectric crystals formed of, for example, barium titillate or cinnabar. Other types of ultrasonic crystal oscillators can also be used. For example, organic electrets such as polyvinylidene difluoride and vinylidene fluoride-trifluoro-ethylene copolymers can also, be used in the ultrasonic transducer 124. The reduced diameter, inner catheter shaft 23 extends through the outer sheath 21, and is attached to the drive unit 127. The drive cable 22 extends through the inner shaft 23 and is engaged to a motor drive shaft (not shown) within the drive unit 127. Exemplary preferred imaging device constructions usable with the present invention may be found in U.S. Pat. No. 5,000,185, U.S. Pat. No. 5,115,814, U.S. Pat. No. 5,464,016, U.S. Pat. No. 5,421,338, U.S. Pat. No. 5,314,408, and U.S. Pat. No. 4,951,677, each of which is expressly and fully incorporated herein by reference.

As illustrated in FIG. 2, the image subsystem 120 implements a pullback approach using the drive unit 127 to longitudinally translate the inner shaft 23, and thus, the drive cable 22 and associated imaging element 124 (and specifically, an ultrasound transducer), in relation to the outer sheath 21. The drive unit 127 also rotates the ultrasound transducer 124 (e.g., at thirty or sixty revolutions a minute), such that the imaging device 122 is able to retrieve image data representing two-dimensional slices of the subject volume. An exemplary preferred drive unit, and methods for using the drive unit, is disclosed in U.S. Pat. No. 6,292,681, which is fully and expressly incorporated herein by reference.

The image processor 126 generally comprises a processor unit 125, a transmitter 121, and a receiver 123. The processor unit 125 activates the transmitter 121 such that the transmitter 121 generates voltage pulses, which may be in the range of 10 to 150 volts, for excitation of the transducer 124. The voltage pulses cause the transducer 124 to project ultrasonic waves into the subject volume. As discussed, the illustrated imaging subsystem 120 is operated using a pullback method. Therefore, the drive unit 127 rotates the transducer 124 and pulls back the transducer 124 proximally towards the drive unit 127 as the transducer is projecting ultrasonic waves into the volume. As a result, the imaging subsystem 120 is able to gather two-dimensional slices of image data for the volume. In a preferred embodiment, the gathering of the two-dimensional slices of image data is gated, e.g., the gathering of image slices is timed relative to cardiac activity or to respiration, and each slice is gathered at substantially the same point in the heart or the respiration cycles. The two-dimensional slices are ultimately aggregated to form a reconstructed, three-dimensional image of the volume. In another embodiment, slices of image data are gathered in sets of slices, such as, sets of thirty or sixty slices. With this embodiment, corresponding slices in each set are matched together in order to form a reconstructed, four-dimensional image of the volume (i.e., a dynamic three-dimensional image that moves over time, e.g., for showing the beating of the heart). For example, the first slices of each set are grouped and displayed together, the second slices of each set are grouped and displayed together, and so on. Tissue, including tissue forming anatomic structures, such as heart, and internal tissue structures and deposits or lesions on the tissue, will scatter the ultrasonic waves projected by the transducer 124. The scattered ultrasonic waves return to the transducer 124. The transducer 124 converts the scattered ultrasonic waves into electrical signals and relays the signals to the receiver 123. The receiver 123 amplifies the electrical signals and subsequently relays the amplified signals to the processor unit 125.

The processor unit 125 digitally processes the signals using known algorithms, such as, e.g., conventional radar algorithms. One suitable algorithm that the processor unit 125 may used is based upon the direct relationship that elapsed time ($\Delta t$) between pulse emission and return echo has to the distance (d) of the tissue from the transducer is expressed as follows: $d=\Delta t/2v$, where v is the speed of sound in the surrounding media. After processing the signals, the processor unit 125 transmits the processed signals, i.e., the image data, to the registration processor 110 of the registration subsystem 102.

As an alternative to the pull back approach, the transducer 124 may be operated without rotation such as in a phased-array arrangement, as shown in U.S. Pat. No. 4,697,595, U.S. Pat. No. 4,706,681, and U.S. Pat. No. 5,358,148, which are all hereby fully and expressly incorporated herein by reference. With the phased-array arrangement, each gathered image is a full image of the volume, rather than the two-dimensional slices gathered using the pull back approach. In this case, a four-dimensional image can be generated simply by operating the phased-array arrangement over time.

A location element 128 is also provided on the distal end of the imaging device 122, and specifically, the distal end of the shaft 23, such that it follows the axial movement of the ultrasound transducer 124 when pulled back. Preferably, the location element 128 is placed adjacent the ultrasound transducer 124. The location element 128 is coupled to a location processor 108, which receives data regarding the location, including orientation, of the location element 128 within the subject volume. The location processor 108 transmits the location data to the registration processor 110. Details of the location processor 108 will be discussed herein.

2. Mapping Subsystem

The mapping subsystem 140 is utilized to identify a target site or sites for treatment within the subject volume. For example, the mapping subsystem 140 is used to locate aberrant conductive pathways, i.e., target sites, within the heart. The aberrant conductive pathways typically constitute irregular patterns called dysrhythmias. Here, the mapping subsystem 140 identifies regions along these pathways, called foci, which are then ablated using the treatment delivery subsystem 160 to treat the dysrhythmia.

Figure 3:
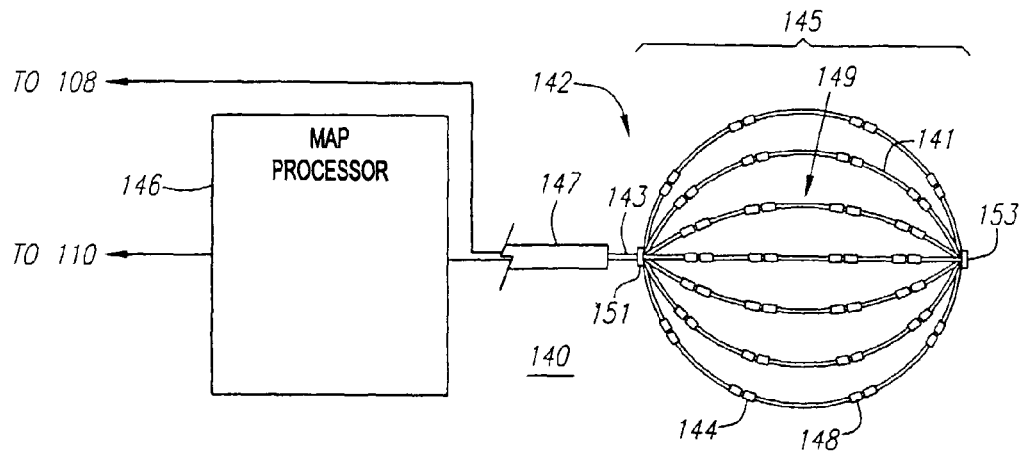
FIG. 3 is a block diagram of a mapping subsystem used in the treatment system of FIG. 1.

FIG. 3 illustrates one preferred embodiment of the mapping subsystem 140. The mapping subsystem 140 includes the map processor 146 coupled to the mapping device 242. The mapping device 142 has a catheter body 143 with distal and proximal ends. On the proximal end, a handle (not shown) is provided that includes connectors (not shown) to couple the mapping device 142 with the map processor 146.

The distal end of the mapping device 142 includes a structure 145 that carries the mapping elements 144. The mapping elements 144 are preferably electrodes. The embodiment in FIG. 3 includes a three-dimensional mapping element carrying structure 145 that takes the form of a basket. The structure 145 may, however, have any configuration that is suitable for carrying mapping elements 144, such as a helical structure or a linear structure. Alternatively, the structure 145 may comprise several catheters, rather than the one shown in FIG. 3. These multiple catheters may be distributed in any configuration suitable for three-dimensional mapping. As shown, the structure 145 comprises a base member 151 and an end cap 153. Generally flexible splines 141 extend in a circumferentially spaced relationship between the base member 151 and the end cap 153, and also define a space 149. The splines 148 are preferably connected between the base member 151 and the end cap 153 in a resilient, pretensed condition. Therefore, the splines 141 are preferably constructed from a resilient, inert material such as Nitinol metal or silicone rubber. In one embodiment, eight splines 141 form the basket structure 145. It should be appreciated that either additional or fewer splines 141 may be utilized depending on the particular application. Additionally, in the illustrated embodiment, each spline 141 is shown as carrying eight mapping elements 144. It should likewise be appreciated that additional or few mapping elements 144 may be carried on each spline 141.

A sheath 147 is provided that is slidable over the catheter body 143 of the mapping device 142. The sheath 147 has an inner diameter that is greater than the outer diameter of the catheter body 143. The sheath 147 may be manufactured from a biocompatible plastic material, such as, e.g., polyurethane. The sheath 147 is slidable distally to cover, i.e., capture and collapse, the structure 145, thereby resulting in a lower profile for the mapping device 142. When the sheath 147 covers the structure 145, the lower profile of the mapping device 142 facilitates the introduction and placement of the structure 145 within the subject volume. When desired, the sheath 147 is slid proximally to remove the compression force the sheath 147 was placing on the structure 145. As a result, the structure 145 opens to assume its uncompressed shape, which, in the illustrated embodiment, is a basket shape. Other devices are also capable of being inserted into the subject volume by using the sheath 147, including the imaging device 122 and the treatment device 162, as will be described in further detail below.

When the mapping device 142 is deployed within, e.g., the heart chamber, the structure 145 holds the mapping elements 144 against the endocardial surface. The resilient nature of the splines 141 of the structure 145 enables the splines 141 to conform and bend to the tissue they contact, thereby placing the mapping elements 144 in direct contact with body tissue. The mapping elements 144 then detect data from the tissue that is used to identify target sites for treatment. In the illustrated embodiment, the mapping elements 144 record the electrical potentials in myocardial tissue. Signals corresponding to the recorded electrical potentials are transmitted to the map processor 146.

The map processor 146, in turn, derives the activation times, the distribution, and the waveforms of the potentials recorded by the mapping elements 144, using known algorithms, to determine any irregular electrical potentials. After the map processor 146 identifies the irregular electrical potentials, the map processor 146 identifies which particular mapping element 144 recorded a specific, irregular electrical potential. An irregular electrical potential corresponds to a target site, and the mapping element 144 that recorded that potential is the mapping element 144 nearest the target site. Thus, the map processor 146 identifies a target site by identifying an irregular electrical potential, identifying the mapping element 144 that recorded the potential, and identifying the target site within the subject volume by reference to that mapping element 144. The map processor 146 then transmits the localized mapping data to the registration processor 110 of the registration subsystem 102. Further details for the deployment and structures of the mapping subsystem 140 are described in U.S. Pat. No. 5,636,634 and U.S. Pat. No. 6,233,491, all of which are hereby fully and expressly incorporated herein by reference. Also, further details for systems and methods for the determination of irregular electrical potentials in order to identify target sites for treatment are described in U.S. Pat. No. 6,101,409, U.S. Pat. No. 5,833,621, U.S. Pat. No. 5,485,849, and U.S. Pat. No. 5,494,042, all of which are hereby fully and expressly incorporated herein by reference.

Additionally, location elements 148 are provided on the structure 145, which each location element 148 in close proximity or adjacent a mapping element 144. The location elements 148 are coupled to the location processor 108, which receives data regarding the location, including orientation, of each location element 148 within the subject volume. Alternatively, rather than mounting the location element 148 on the mapping device 142, the location element 148 can be located on a roving probe. In this case, the locations of the mapping elements 144 can be determined by determining the proximity between the location element 148 on the roving probe and one or more mapping elements 144. Further details on the use of a roving probe mounted location element to locate and register mapping elements are disclosed in U.S. patent application Ser. No. 10/147,179, entitled "Systems and Methods for Guiding and Locating Functional Elements on Medical Devices Positioned in a Body," and filed on Oct. 24, 2001, which is fully and expressly incorporated herein by reference.

The location processor 108 transmits the location data to the registration processor 110. Details of the location processor 108 will be discussed herein.

3. Treatment Delivery Subsystem

Figure 4A:
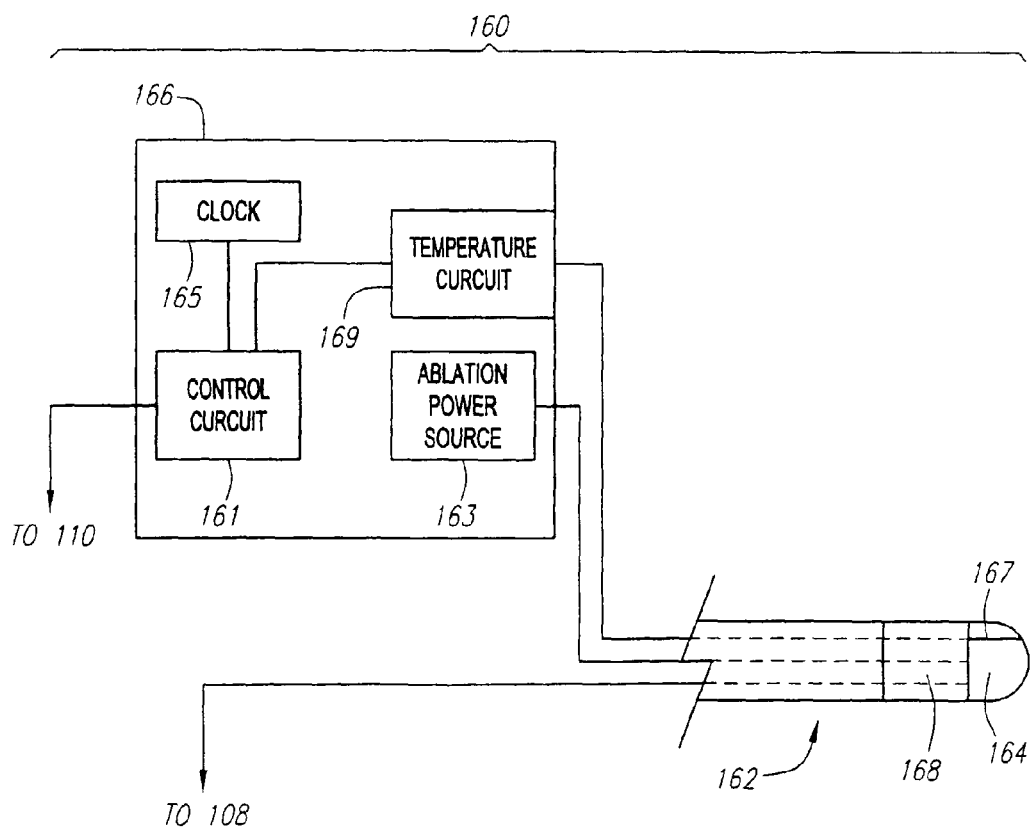
FIG. 4a is a block diagram of a treatment delivery subsystem used in the treatment system of FIG. 1.
Figure 4B:
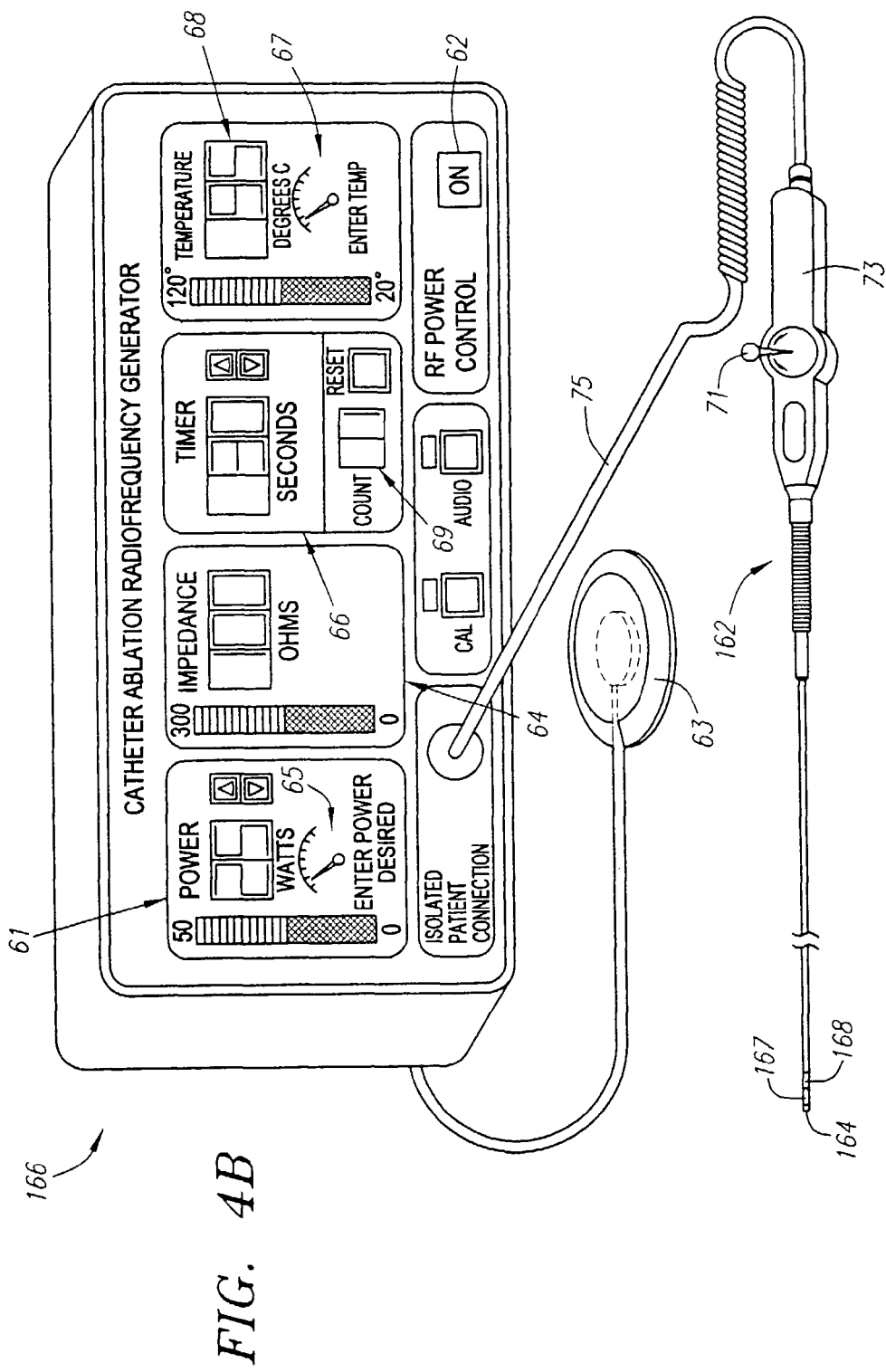

The treatment delivery subsystem 160 is utilized to treat the targeted sites identified by the mapping subsystem 140. As illustrated in FIGS. 4a and 4b, a preferred embodiment of the treatment delivery subsystem 160 includes the treatment device 162, that is an ablation catheter, coupled to the treatment delivery source 166. More particularly, the treatment delivery source 166 is coupled to the treatment element 164 disposed on a distal end of the treatment device 162. The treatment delivery source 166 is an ablation power generator that includes an ablation power source 163, and the treatment element 164 is an ablation element. In one preferred embodiment, the treatment device 162 is a steerable catheter as described in U.S. Pat. No. 6,233,491, which has been fully and expressly incorporated by reference herein. Accordingly, the treatment device 162 shown in FIG. 4b includes a steering component 71 mounted on a handle 73. A cable 75 connects a proximal end of the handle 73 to the treatment delivery source 166.

Also, the treatment device 162 preferably includes a temperature sensor 167 located near the treatment element 164. When ablation energy is used, the temperature sensor 167 facilitates the delivery of ablation energy to a target site by gathering and transmitting temperature data for the target site to the treatment delivery source 166. A temperature gauge 68 displays the temperature data. Alternatively, the registration subsystem 102 may display the temperature of the tissue surrounding the target site to the user on the display 106.

The ablation energy delivered by the ablation power source 163 is used to ablate target sites identified using the mapping subsystem 140 by heating the targeted tissue. The ablation power source 163 is preferably a radio frequency (RE) generator. Any suitable ablation power source 163 may be utilized, however, including, e.g., a microwave generator, an ultrasound generator, a cryoablation generator, and a laser or other optical generator. In the illustrated embodiment, the treatment delivery source 166 delivers radio frequency energy to the treatment element 164 in a controlled manner. To this end, the treatment delivery source 166 comprises a control circuit 161 that controls the amount of ablation energy delivered by the ablation power source 163 to the treatment element 164, and a temperature circuit 169 for facilitating the input of temperature sensing data from the temperature sensor 167 into the control circuit 161. A power control input 65 is used by the user to set the ablation energy desired to be delivered by the treatment delivery source 166. A clock 165 is also provided to track the time elapsed during the delivery of ablation energy, and a counter 69 is provided to display the elapsed time. A timer input 66 is coupled to the clock 165, and allows a user to input the desired time of delivery of energy. The actual ablation energy delivered by treatment delivery source 166 is reported by a power meter 61. Also, an impedance meter 64 coupled to the control circuit 161 measures contact between the treatment element 164 and tissue. An ablation power control button 62 allows the user to place the source 166 in a power "on" or "off" orientation. Further details on the use and structure of a suitable treatment delivery source using ablation energy are disclosed in U.S. Pat. No. 5,383,874 to Jackson, et al., which is expressly and fully incorporated herein by reference.

A location element 168 is provided on the distal end of the treatment device 162, and preferably in close proximity or adjacent to the treatment element 164. Also, the location element 168 may be incorporated into the treatment element 164, thereby eliminating the need for a physically separate location element 168. The location element 168 is coupled to the location processor 108 and provides data regarding the location, including orientation, of the location element 168 within the subject volume to the location processor 108. The location processor 108 transmits the location data to the registration processor 110. Details of the location processor 108 will be discussed herein.

4. Registration Subsystem

The registration subsystem 102 of the system 100 includes the location processor 108, registration processor 110, and the location elements 128, 148, and 168. The location processor 108 is preferably incorporated into the registration subsystem 102, but may be a stand-alone subsystem that is coupled to the registration subsystem 102. In either case, the location processor 108 is coupled to the registration processor 110 of the registration subsystem 102. The location elements 128, 148, and 168 can be electrically coupled to the location processor via wires. Alternatively, wireless location sensors, such as, e.g., electromagnetic or magnetic resonant transducers, electronic emitters, infra- or near-infrared emitters, can be used as any of the location elements 128, 148, or 168. In this case, a link between the location elements 128, 148, or 168 and the location processor 108 can be a wireless link. For any of the location elements 128, 148, or 168, the location processor 108 may use ultrasound, magnetic fields, or optical means, to track the position of any of the location elements 128, 148, or 168 with respect to the three-dimensional coordinate system, thereby enabling the registration of the image data, mapping data, or location of the treatment element 164, respectively, to the three-dimensional coordinate system.

The location processor 108 processes and provides position specific information in various ways. In the embodiment shown in FIG. 5, the location processor 108 utilizes ultrasound to determine the absolute location of a location element 168(1) within the three-dimensional coordinate system of the subject volume. Here, the location element 168(1) is an ultrasonic transducer. Suitable transducers include, but are not limited to, phased array transducers, mechanical transducers, and piezoelectric crystals. Triangulation techniques are utilized in order to render an absolute location, including orientation, of the location element 168(1) with respect to the three-dimensional coordinate system. Since the location element 168(1) is placed in close proximity to the treatment element 164, or is incorporated into the treatment element 164, the absolute location including orientation of the treatment element 164 is also determined.

Figure 5:
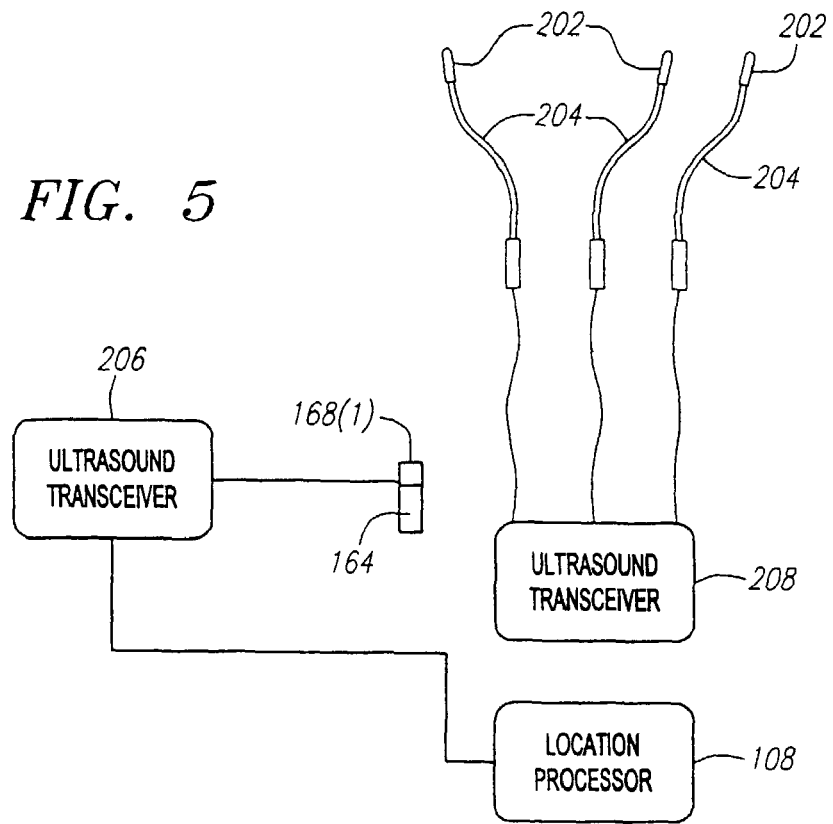
FIG. 5 is a block diagram of a an ultrasound locating portion of a registration subsystem used in the treatment system of FIG. 1.

To determine the absolute location of the location element 168(1), the time of flight of a sound wave transmitted from the location element 168(1) relative to reference transducers 202 located on reference catheters 204 may be determined. The reference transducers 202, instead of being disposed on catheters, may alternatively be placed at other locations in or on the body, such as, e.g., on a patient's chest or at fixed points away from the body. Additionally, although three reference transducers 202 are illustrated in FIG. 5, both a smaller number or a larger number of reference transducers may be utilized.

In embodiments of the location processor 108 having reference transducers 202 that are disposed on reference catheters 204, the reference catheters 204 may be placed at locations outside the subject volume, placed outside of the body, or inserted into the subject volume in order to provide a plurality of reference points within the volume. Although illustrated as being towards the distal tip of the catheters 204, it will be appreciated that the reference transducers 202 are capable of being disposed at any point along the length of the reference catheters 204.

The location element 168(1) is preferably in operable connection with an ultrasound transceiver 206. The reference transducers 202 are preferably coupled to an ultrasound transceiver 208. The location processor 108 is coupled to both of the ultrasound transceivers 206, 208. In an alternative embodiment, the location element 168(1) and the reference transducers 202 may be coupled to a single ultrasound transceiver, thereby eliminating the need for two ultrasound transceivers. In another embodiment, the location processor 108 may incorporate the ultrasound transceivers, thereby eliminating the need for separate transceivers 206, 208.

Returning to FIG. 5, the location processor 108 preferably includes control circuits that cause the location element 168(1) and the reference transducers 202 to vibrate and produce ultrasound waves, by controlling the transceivers 206, 208. For example, the transceivers 206, 208 transmit and receive the ultrasonic signals that are sent to and received from the location element 168(1) and the transducers 202.

The ultrasound signals that are transmitted by the location element 168(1) and the transducers 202 travel through the patient's body. Subsequently, a portion of the signals generated by the location element 168(1) will be reflected back from a bodily structure and impinge, i.e., be received by, the location element 168(1). These signals are not, however, processed because location element 168(1) is not in listening mode at this time. Transducers 202 are, however, in listening mode. When in listening mode, the location element 168(1) will also receive ultrasound signals that were generated by the transducers 202. The location element 168(1) generates electrical signals corresponding to the ultrasound signals received from transducers 202, and then transmits the electrical signals back to the location processor 108 via the ultrasound transceiver 206. In a like manner, the transducers 202 will receive signals generated by the location element 168(1). The transducers 202 are also capable of generating electrical signals representing the received signals and transmitting the electrical signals back to the location processor 108 via transceiver 208.

The location processor 108 analyzes electrical signals corresponding to ultrasound signals received by both the location element 168(1) and the reference transducers 202 in order to triangulate the position and orientation of the location element 168(1). The location processor 108 preferably uses an algorithm that compensates for the known velocity of sound in the blood pool when making the calculations, if reference transducers 202 are placed within the body along with the location element 168(1). Using these calculations, the location processor 108 employs triangulation methods and determines a precise three-dimensional location and orientation, i.e., an absolute location, of the location element 168(1) with respect to the three-dimensional coordinate system that is provided by the reference transducers 202. Preferably, the location processor 108 performs these calculations on a continual basis in order to enable the real time tracking of the location element 168(1) within the patient's body.

Further examples of ultrasonic triangulation techniques and systems suitable for implementation with the precise location tracking subsystem are disclosed in U.S. Pat. No. 6,027,451, entitled "Method and Apparatus for Fixing the Anatomical Orientation of a Displayed Ultrasound Generated Image," and U.S. Pat. No. 6,070,094, entitled "Systems and Methods for Guiding Movable Electrode Elements Within Multiple-Electrode Structures," which are expressly and fully incorporated herein by reference.

Figure 6:
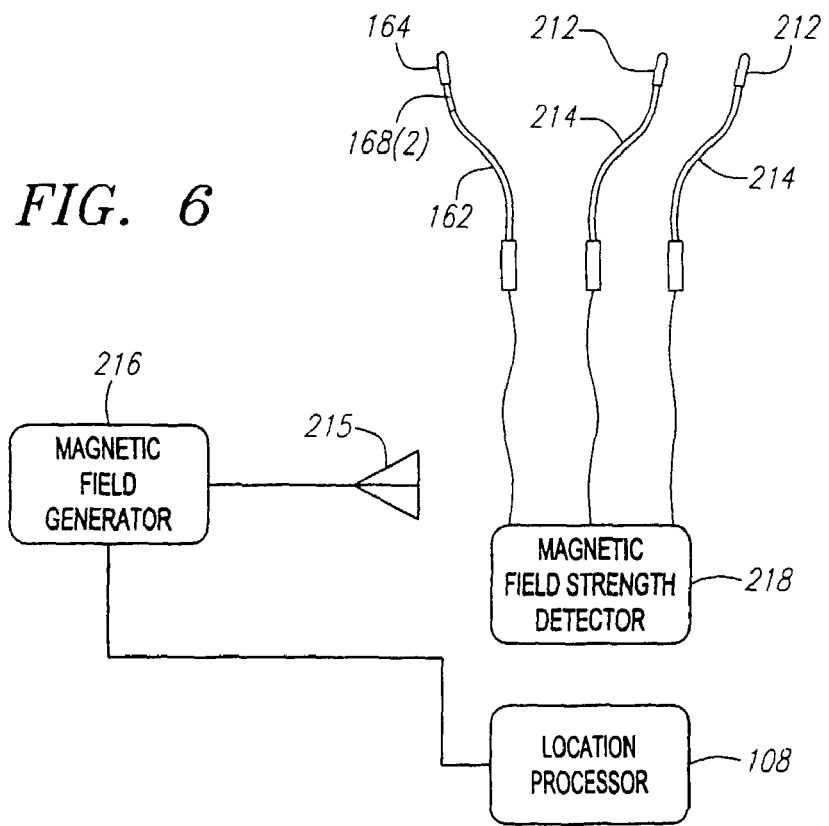
FIG. 6 is a block diagram of an a magnetic locating portion of a registration subsystem used in the treatment system of FIG. 1.

In another embodiment, shown in FIG. 6, magnetic field locating techniques are utilized by the location processor 108 to track the absolute position of a location element 168(2). Here, the location element 168(2) may be a magnetic sensor, and is preferably an array of magnetic sensors. For example, the location element 168(2) may be an array of three or six magnetic coil sensors, with each coil sensor oriented to provide one of the x, y, z, yaw, roll, and pitch coordinates for the location element 168(2). Additionally, the location element 168(2) may be separate from the treatment element 168, as illustrated in FIG. 6, or the treatment element 168 may incorporate a magnetic sensor, thereby eliminating the need for a separate and discrete location element 168(2). Reference magnetic sensors 212 are placed either in the subject volume, on the body, or on some location outside of the body. When placed within the subject volume, each reference sensors 212 is preferably disposed on a distal end of a reference catheter 214.

An antenna 215 transmits magnetic fields that are received by the sensors. The antenna 215 is coupled to a magnetic field generator 216. The magnetic field generator 216 originates the signals that the antenna 215 transmits to the location element 168(2) and the reference sensors 212. The magnetic field generator 216 is preferably coupled to location processor 108, which controls the operation of generator 216.

In a preferred embodiment, the antenna 215 transmits three orthogonal magnetic fields. The location element 168(2), in this embodiment, comprises a plurality of coils configured to detect the orthogonal magnetic fields transmitted by antenna 215. After detecting the orthogonal magnetic fields transmitted by antenna 215, location element 168(2) transmits a signal to magnetic field strength detector 218. The magnetic field strength detector 218 may be a separate unit that is coupled to the location processor 108. In another embodiment, however, the magnetic field strength detector 218 may be implemented as an integral portion of the location processor 108, rather than as a separate unit. The magnetic field strength detector 218 relays the signal received from the location element 168(2) to the location processor 108.

The location processor 108 employs an algorithm to compute the distance vector between the center of the antenna 215 and the location element 168(2). The location processor 108 preferably bases this calculation on the signal received by the location element 168(2) and the signal transmitted by the antenna 215. The vector is deconstructed into its x, y, and z components, as well as pitch, roll, and yaw data, in order to compute the coordinates and orientation of location element 168(2). The location processor 108 preferably performs the aforementioned calculations continually, and on a real-time basis.

Additionally, the location processor 108 may analyze signals from a number of reference sensors 212 in order to minimize the effects of any motion artifacts on the localization of location element 168(2). As illustrated, the reference sensors 212 are disposed on reference catheters 214 that may be inserted within the body or placed outside the body. Alternatively, the sensors 212 may be placed on an external surface of the body or on a fixed point away from the body entirely. Furthermore, although FIG. 6 shows two reference catheters 214, each having one reference sensor 212, a smaller or larger number than two reference catheters 214 may be used to vary the degree to which the localization of the location element 168(2) is refined. Additionally, each reference catheter 214 may incorporate more than one reference sensor 212 in order to further refine the localization of the location element 168 (2) or to provide enough data to compute the curvature of the catheter 162. For example, if three location elements 168(2) are placed at certain points along catheter 162 then a circle that approximates the catheter curvature can be fitted through these three points. The reference sensors 212 are preferably coupled to magnetic field strength detector 218 and transmit signals, corresponding to received magnetic fields, to the detector 218. The detector 218 is configured to transmit these signals to the location processor 108 in substantially the same manner as previously described with the relay of signals from the location element 168(2). These calculations are preferably performed continually and in real time.

Regardless of whether the location processor 108 utilizes magnetic or ultrasonic waves in determining the location of the location element 168, the location processor 108 provides the positional location data for the location element 168 to the registration processor 110 of the registration subsystem 102. The registration processor 110 is configured to calculate the position of the treatment element 164 based upon the positional data for the location element 168, register that positional data in the three-dimensional coordinate system, and store the positional data for the treatment element 164 in memory 104. Calculating the positional location data for the treatment element 164 in this manner is possible since the location element 168 is placed in close proximity to, or is incorporated in, the treatment element 164. Alternatively, the positional location data for the treatment element 164 can be calculated based upon the position of the location element 168 and the distance between the location element 168 and the treatment element 164. The registration subsystem 102 is configured to output the location of the treatment element 164 on display 106.

The implementation of the location elements 128 and 148 within the registration subsystem 102, and the manner in which the imaging element 124 and mapping elements 144 are respectively located, is similar to the implementation of the location element 168 within the registration subsystem 102 and the manner in which the treatment element 164 is located, as just described, and will thus not be discussed in further detail for purposes of brevity.

5. Overall Operation of the System

Figure 7A:
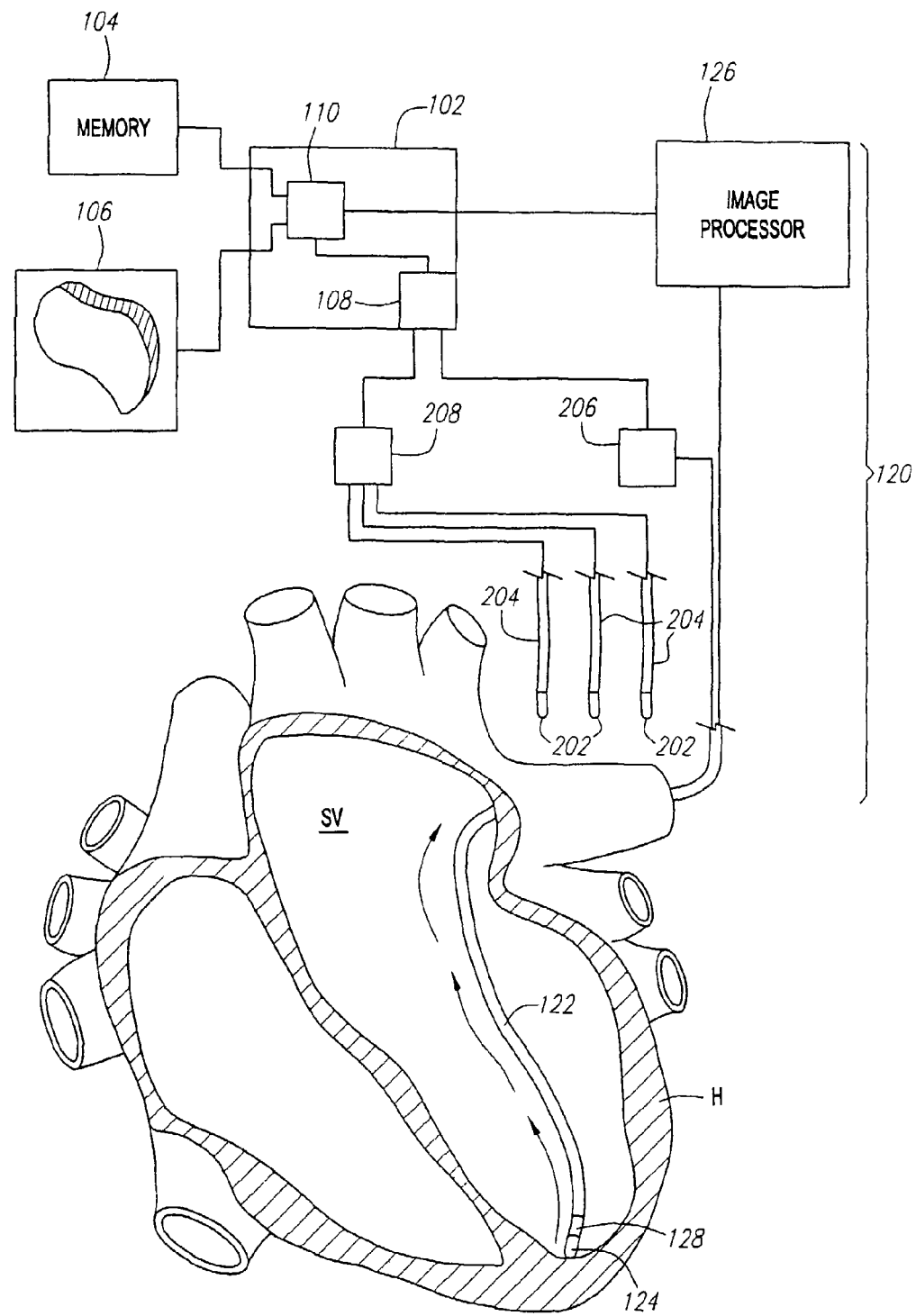
FIG. 7a is a schematic diagram showing the operation of the imaging subsystem and the FIG. 5 registration subsystem within the heart of a patient.

One preferred method of operating the system 100 will now be described. Turning to FIG. 7a, the imaging device 122 having an ultrasonic transducer 124 is introduced into the subject volume SV using known techniques. For example, in one process, a transeptal deployment is utilized. For a procedure in the left atrium using the transeptal deployment, for example, the sheath 147 is first maneuvered into the right atrium. An opening is made through the septum, and the sheath 147 is advanced into the left atrium. The imaging device 122 is then routed through the sheath 147 and into the left atrium. Preferably, the opening is as small as possible, but large enough to allow the passage therethrough of the imaging device 122, via the sheath 147.

The user maneuvers the imaging device 122 in the volume SV until the distal tip touches a distal wall that defines the subject volume SV. The user operates the imaging subsystem 120 to gather image data regarding the subject volume SV. As previously noted, in an embodiment of the imaging subsystem 120 that implements a pull-back approach, multiple two-dimensional image slices of the subject volume SV are gathered. The pullback can be along a rectilinear or curved trajectory. If the trajectory is curved then, in order to determine the curvature, it is preferable to have more than three location elements placed on the imaging device 122. Additionally, the image slices are preferably gathered at the same relative time, such as at the same point in the cardiac cycle. To form four-dimensional images, sets of image slices are gathered. The sets of image slices may be sets of thirty images, for a thirty frame per second imaging rate, or sixty images, for a sixty frame per second imaging rate. The imaging subsystem 120 provides the image data to the registration processor 110 of the registration subsystem 102.

Figure 7B:
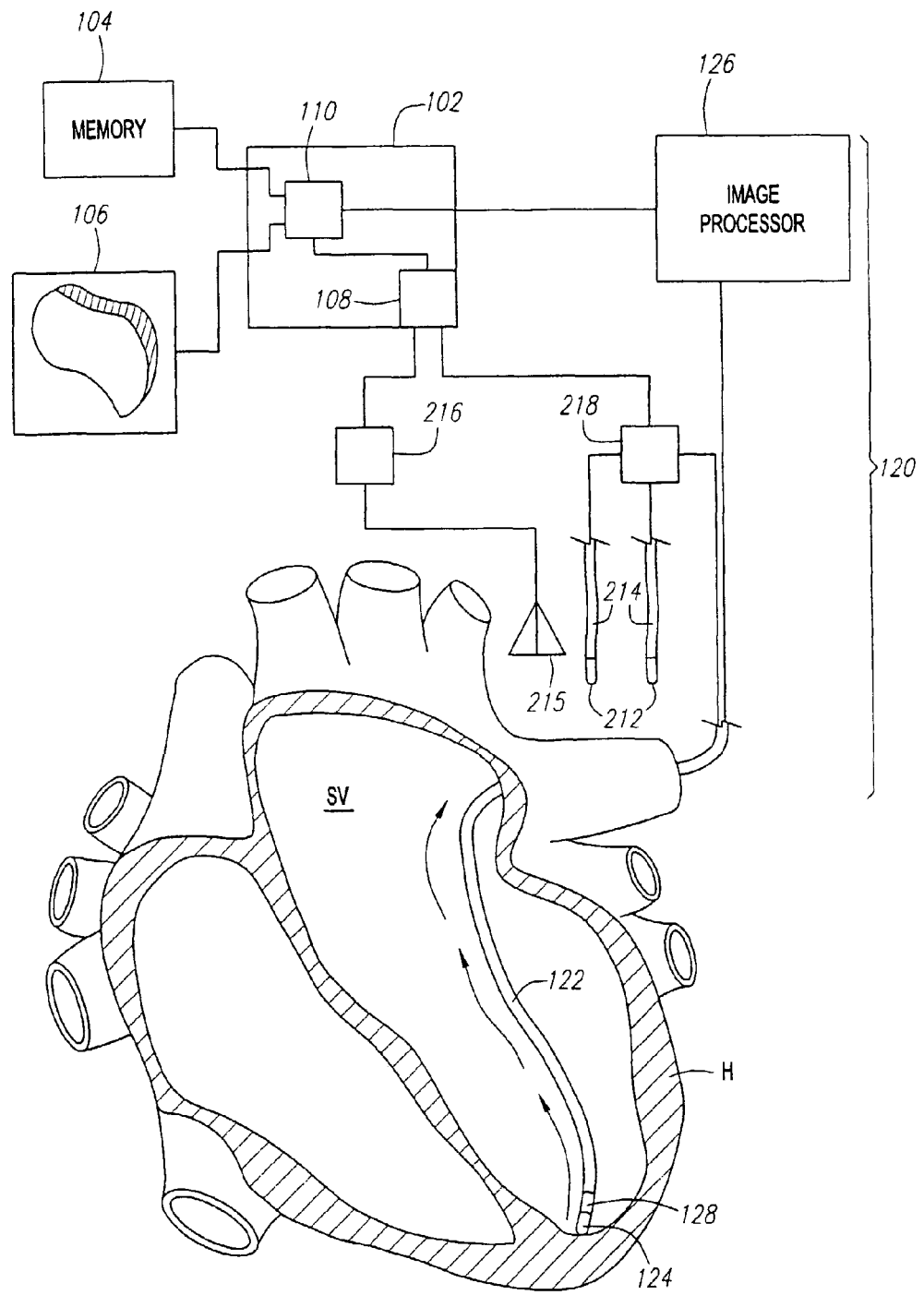
FIG. 7b is a schematic diagram showing the operation of the imaging subsystem and the FIG. 6 registration subsystem within the heart of a patient.

As illustrated in FIG. 7a, the location processor 108 uses ultrasound to track the position of the location element 128 (which in this case will be an ultrasound location element) of the imaging device 122, and reference transducers 202 are used to provide reference points for the location processor 108. The user may place reference transducers 202 within the subject volume SV, as well as outside the body. As shown in FIG. 7b, magnetic fields are used by the location processor 108 (which in this case will be a magnetic location element) to track the location element 128, and the user places the antenna 215 at some point outside the body to provide a reference signal. The user may also introduce reference sensors 212 into the subject volume SV, or place reference sensors 212 outside the body, to refine the localization of location element 128. With either process, the reference transducers 202, or the reference sensors 212 and antenna 215, are preferably left in place for the other steps of the process to allow for additional locating of the location elements 148 and 168.

After receiving the position of the location element 128 on the imaging device 122 from the location processor 108, the registration processor 110 registers the image data to a three-dimensional coordinate system, stores the registered image data in memory 104, and eventually presents the image data, as a reconstructed three-dimensional or four-dimensional representation of the subject volume SV, on display 106. For example, in one process, the imaging device 122 is left within the volume SV during the following steps, and provides continually updated image data regarding the subject volume SV to the imaging subsystem 120, which relays that data to the registration processor 110 of the registration subsystem 102. The registration subsystem 102 then updates the reconstructed image of the subject volume SV as the updated image data is provided. The registration subsystem 102 presents the reconstructed representation in four-dimensions, i.e., the image is dynamic. With a dynamic four-dimensional image of the heart, for instance, activities such as the closure and opening of valves and vessels, atrio-septal defects, and atrio-septal defect closure plugs are displayed in animated form to the user.

In another aspect of the method, the imaging device 122 is removed from the volume SV prior to the following steps. The following steps may still be accomplished by reference to the previously acquired, and registered, three-dimensional or four-dimensional image.

In another preferred embodiment, the imaging device 122 is a real-time three-dimensional imaging device such as an optical camera or a three-dimensional real-time ultrasound catheter. Such embodiment does not necessarily require the pullback step because it already provides three-dimensional renderings of the volume SV real-time. If imaging of extended portions of the volume SV is required then pullback of the real-time imaging device may be necessary. As in the previous embodiment, one or more location elements 128 may be placed on the imaging device.

Figure 8A:
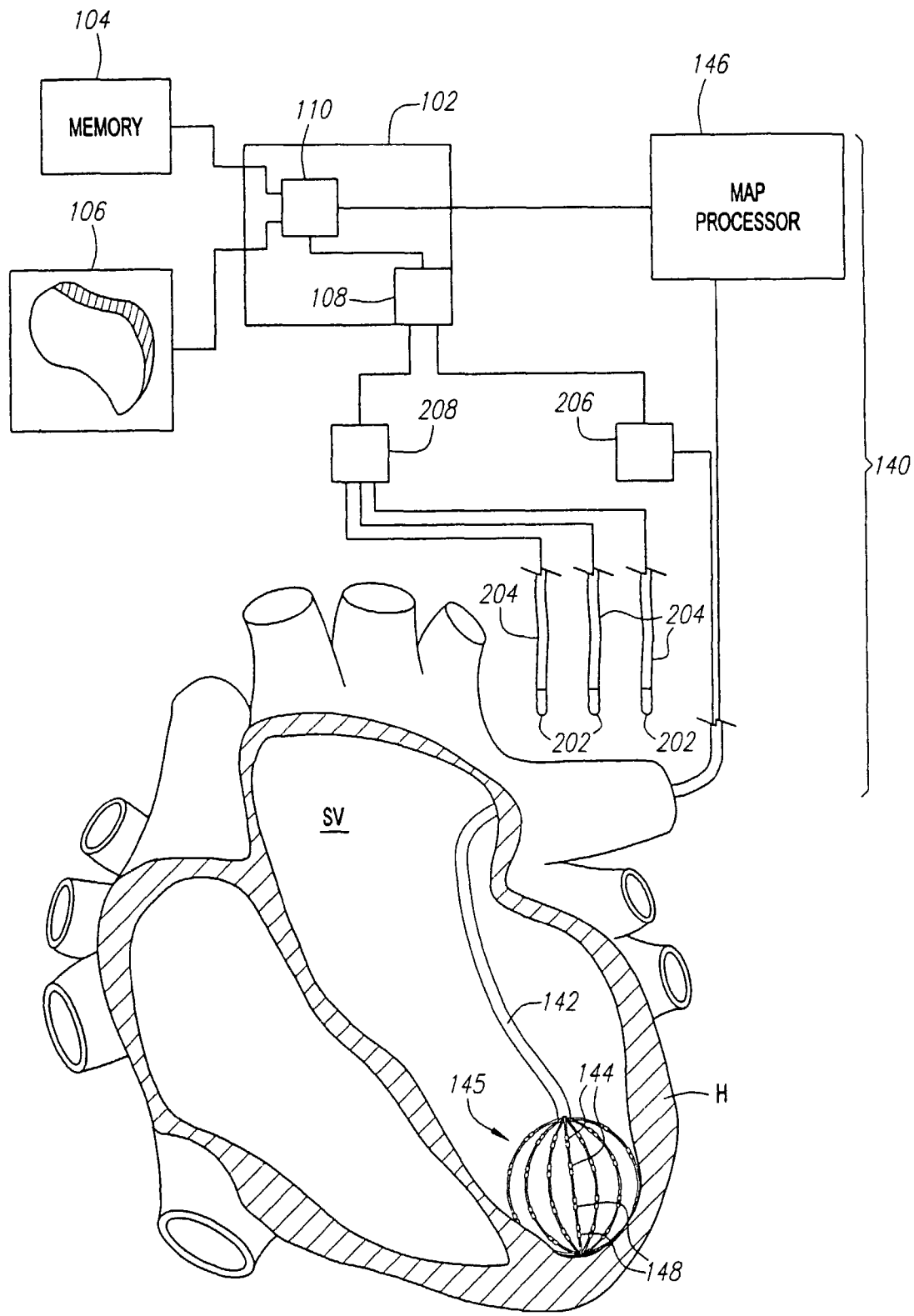
FIG. 8a is a schematic diagram showing the operation of the mapping subsystem and the FIG. 5 registration subsystem within the heart of a patient.
Figure 8B:
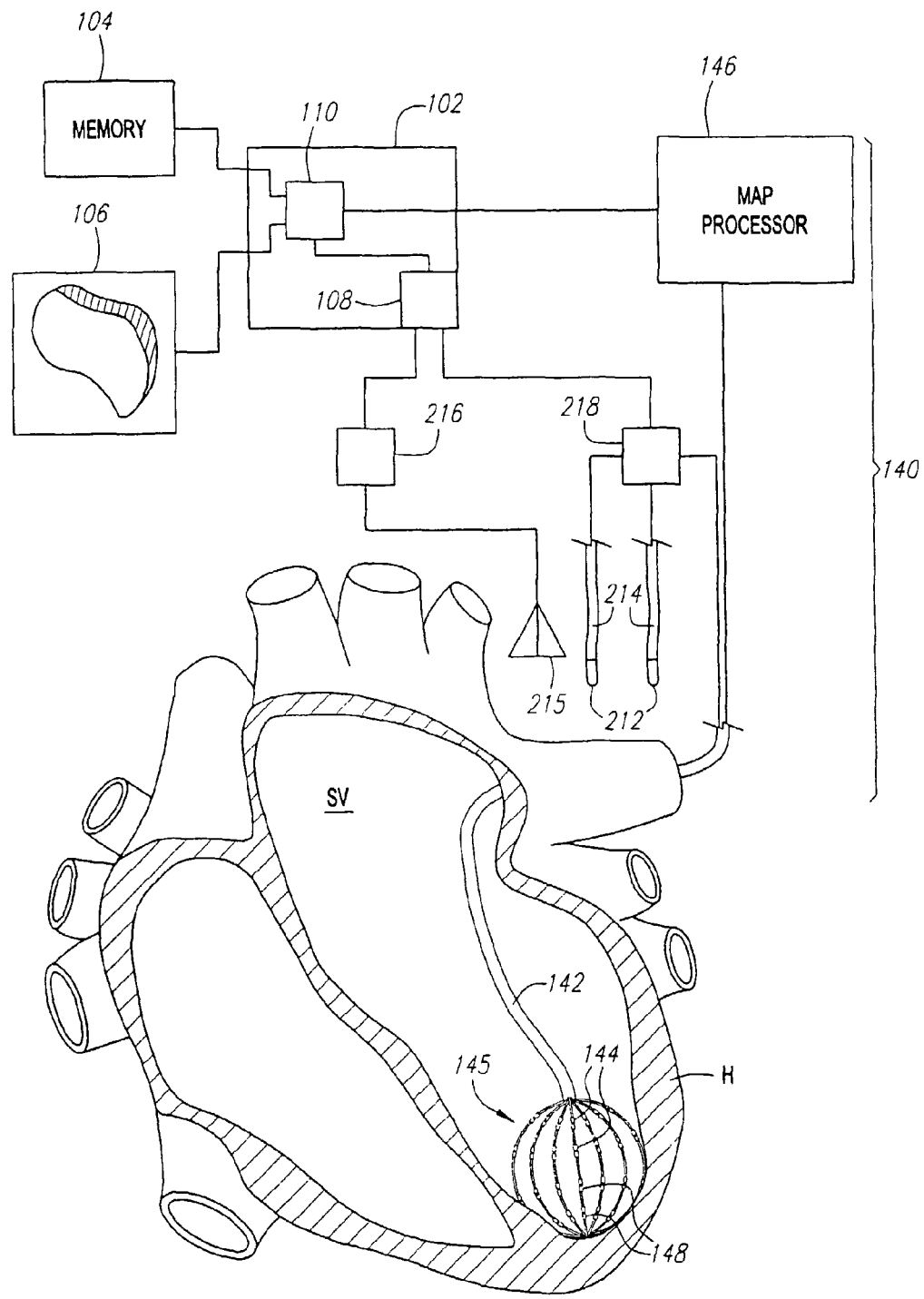
FIG. 8b is a schematic diagram showing the operation of the mapping subsystem and the FIG. 6 registration subsystem within the heart of a patient.

In addition to gathering and processing image data regarding the subject volume SV, the system 100 is used to acquire and process mapping data indicating any target sites for treatment within the subject volume SV. Turning to FIGS. 8a and 8b, the mapping device 142 is introduced into the subject volume SV. Specifically, the mapping device 142 is inserted through the sheath 147, and therefore the opening, through which the imaging device 122 was originally inserted.

Initially, the mapping device 142 is introduced into the subject volume SV with the sheath 147 (see FIG. 3) covering the structure 145. After the user places the mapping device 142 at a desired location in the subject volume SV, the sheath 147 is moved proximally to allow the structure 145 to expand. This results in the mapping elements 144 being placed in contact with tissue. The map processor 146, which is coupled to the mapping device 142, is then operated to receive and analyze data regarding tissue surrounding the mapping elements 144. After receiving the mapping data, the map processor 146 relays the mapping data to the registration processor 110 of the registration subsystem 102. Additionally, the location processor 108 provides the location of location elements 148 within the three-dimensional coordinate system to the registration processor 110. FIG. 8a illustrates the use of the location processor 108 that uses ultrasound to determine the positions of the location elements 148, whereas FIG. 8b illustrates the use of the location processor 108 that uses magnetic fields to determine the positions of the location elements 148. After receiving the positional data for the location elements 148, the registration processor 110 registers the mapping data in the same three-dimensional coordinate system within which the processor 110 registered the image data from the imaging subsystem 120. The registration processor 110 may store the registered mapping data within memory 104. As illustrated in FIGS. 8a and 8b, the registration processor 110 then displays the registered mapping data, along with the image data, i.e., the reconstructed image of the subject volume, on the display 106.

Figure 10:
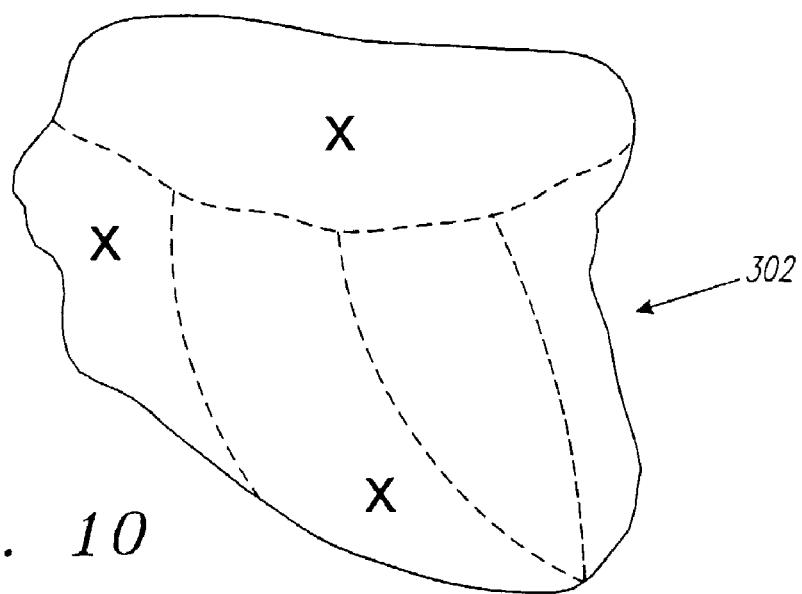
FIG. 10 is an illustration of a reconstructed three-dimensional image having superimposed thereon three-dimensional mapping data.
Figure 11:
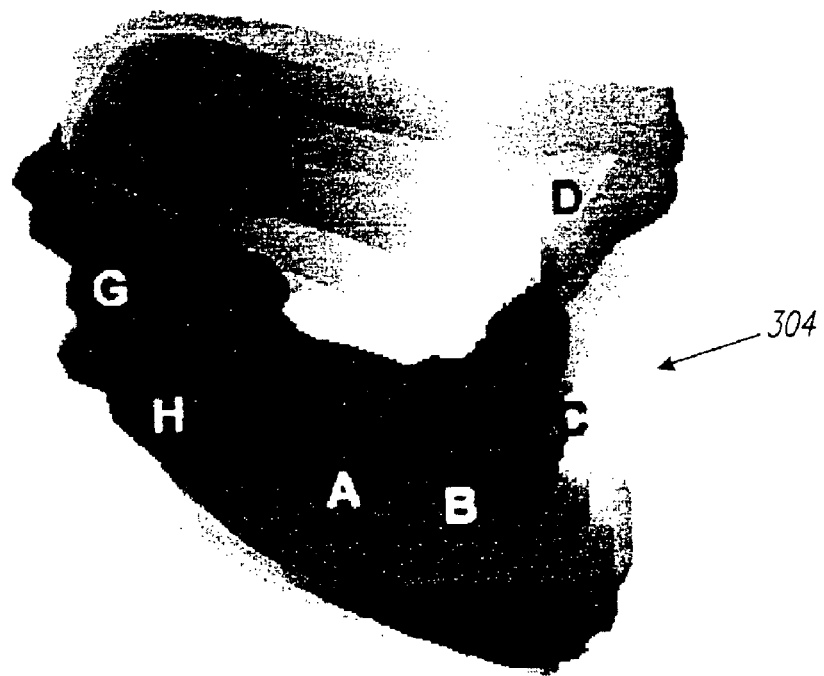
FIG. 11 is an illustration of a reconstructed three-dimensional image along with three-dimensional mapping data wherein the mapping data is presented in varying colors.

In one aspect of this method, the mapping data is superimposed over a reconstructed three-dimensional image of the subject volume. In another aspect of this method, the mapping data is superimposed over a reconstructed four-dimensional image of the subject volume. FIG. 10 illustrates a reconstructed three-dimensional image 302 of the subject volume having superimposed thereon target point data, which are represented by discrete points X. FIG. 11 illustrates a reconstructed three-dimensional image 304 of the subject volume having superimposed three-dimensional mapping data where the positional data is displayed in various colors (shown as different shades). Each color represents the time delays sensed by the mapping elements 144, and a user is able to identify a target site based on a particular color, or pattern of color such as a swirling pattern. Alternatively, the mapping data can be four-dimensional, i.e., dynamical three-dimensional mapping data that changes over time. FIG. 11 also shows the relative positions of the splines 148 of the mapping device 142 with the letters A through F. A four-dimensional reconstructed image having three-dimensional mapping data superimposed thereon would look similar to FIG. 10 and FIG. 11, respectively, but the image would be animated.

Figure 9A:
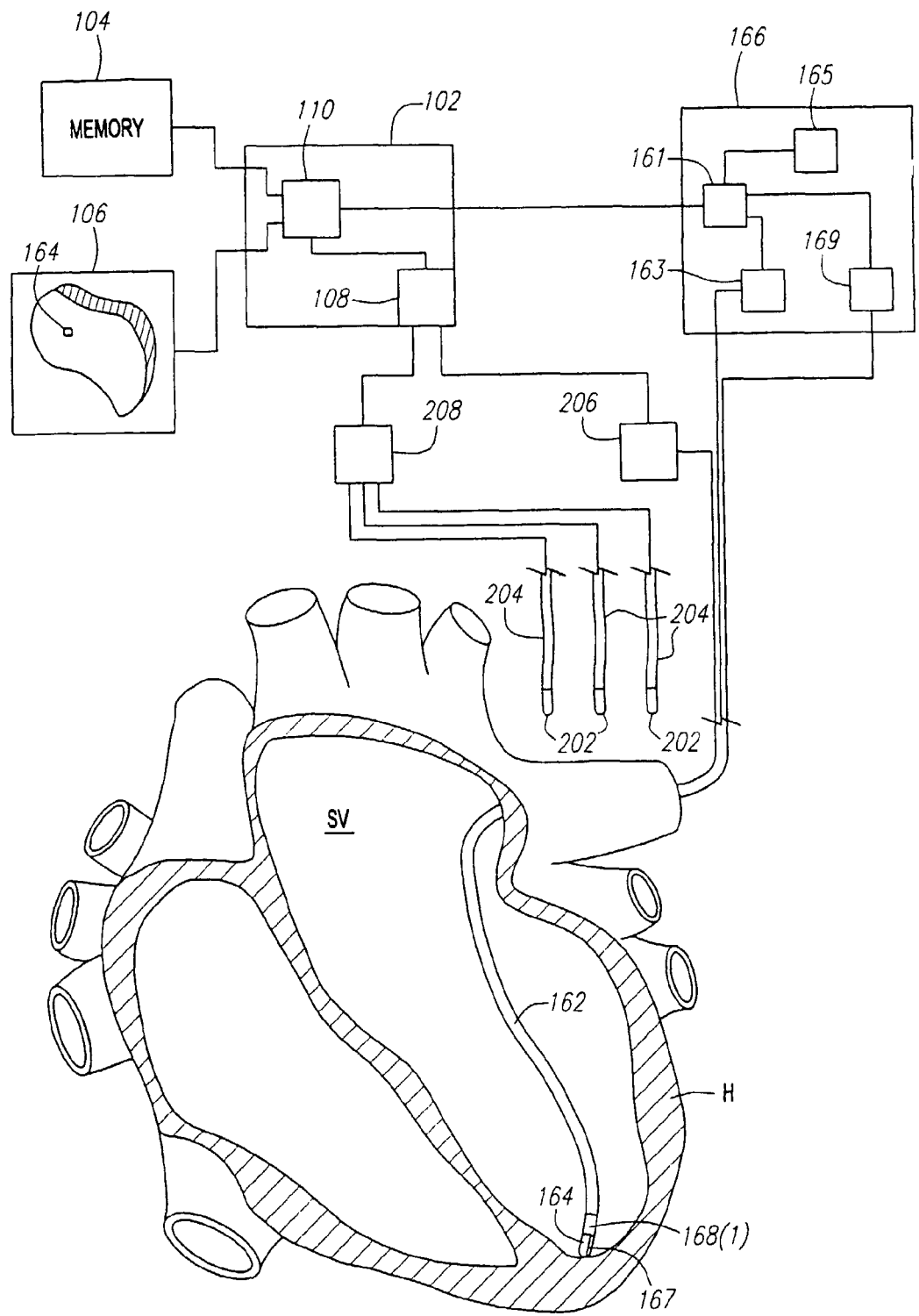
FIG. 9a is a schematic diagram showing the operation of the treatment delivery subsystem and the FIG. 5 registration subsystem within the heart of a patient.
Figure 9B:
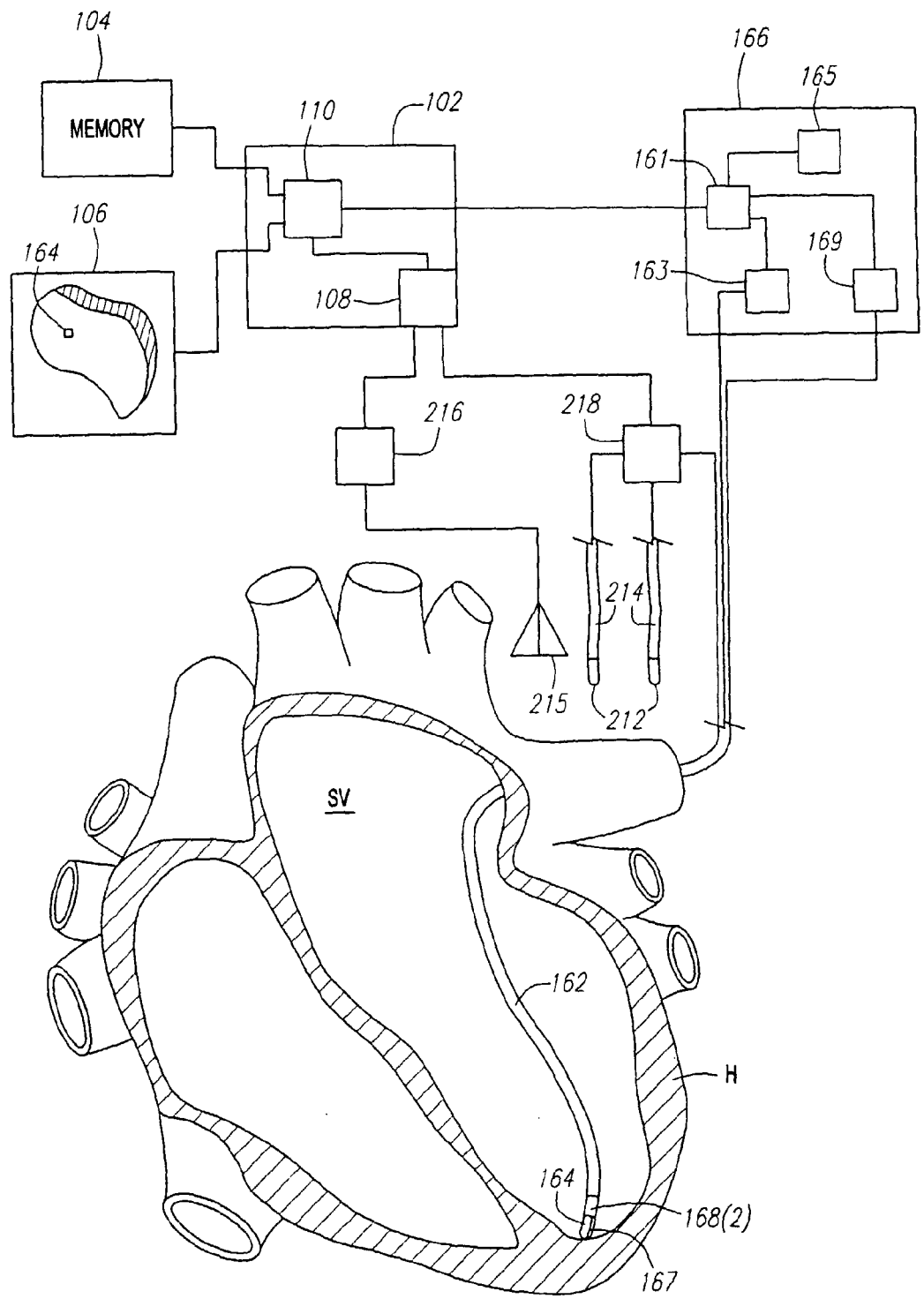
FIG. 9b is a schematic diagram showing the operation of the treatment delivery subsystem and the FIG. 6 registration subsystem within the heart of a patient.

Reference is now made to FIGS. 9a and 9b, which shows the processes wherein the location processor 108 utilizes ultrasound (FIG. 9a) or magnetic fields (FIG. 9b) to determine the location of location element 168 for purposes of navigating the treatment device 162. To guide a user in placing a treatment device 162, and specifically a treatment element 164 on the device 162, at a target site for delivering treatment, the registration processor 110 simultaneously displays the mapping data, the reconstructed image of the subject volume, and the location of the treatment element 164 within the volume on the display 106. Alternatively, the mapping data may not be necessary to be displayed if the user targets certain anatomic aspects of the subject volume SV. By reference to the display 106, the user is able to maneuver the treatment element 164 to a target site, indicated by the displayed mapping data or by another type of target, such as an anatomic landmark.

First, the treatment device 162 is introduced into the subject volume SV. For either of the methods shown in FIG. 9a or 9b, positional data for the location element 168 is continually provided to the location processor 108 as the treatment device 162 is moved within the subject volume SV. The location processor 108, in turn, provides the positional data for the location element 168 to the registration processor 110. As previously discussed, the registration processor 110 determines the positional data for the treatment element 164 based upon the positional data for the location element 168, registers the positional data for the treatment element 164, and display the positional data on a display 106 along with the reconstructed image of the volume SV and, if necessary, the mapping data.

The registration subsystem 102 continually updates the positional data for the treatment element 164 on the display 106, using the aforementioned steps, as positional data for the location element 168 is provided by the location processor 108. By reference to the combined display of the reconstructed three-dimensional or four-dimensional image data, the optional three-dimensional or four-dimensional mapping data, and the positional data for the treatment element 164 on the display 106, the user places the treatment element 164 at a target site. Alternatively, the user may guide the treatment element 164 by only referencing the combined display of the mapping data and the treatment element 164. Optionally, the positional data of the treatment element 164 can be stored in memory 104, and then recalled and displayed on the display 106, so that the physician can view the trajectory of the treatment element 164 as it is moved within the subject volume SV.

Once the user or physician positions the treatment element 164 adjacent a target site, the user or physician is then able to operate the treatment delivery source 166 to deliver treatment to the site. Also, the treatment element 164 may be a therapeutic agent delivery element, rather than an ablation element. In this case, the user delivers a therapeutic agent rather than ablation energy to the target site X. All of the other processing steps with regard to reconstructing a three-dimensional or four-dimensional image of the subject volume SV, or determining the three-dimensional or four-dimensional mapping data within the volume SV, and guiding a user in maneuvering the treatment element 164 to a target site apply equally irrespective of whether the treatment element 164 is an ablation element or a therapeutic agent delivery element.

Returning to the methods shown in FIGS. 9a and 9b, wherein the treatment delivery source 166 includes the ablation power source 163, the user operates the treatment delivery source 166 to controllably deliver ablation energy to target sites. Specifically, the treatment delivery source 166 comprises set point parameters, which can be adjusted when the treatment delivery source 166 is in standby mode. The set point parameters include, among others, the magnitude of the ablation power delivered to the tissue, the desired tissue temperature, and the duration of ablation power delivery.

To this end, the ablation power delivered by the treatment delivery source 166 is set using the power control input 65 coupled to the control circuit 161. The actual ablation power delivered by the treatment delivery source 166 is reported by the power meter 61. During ablation energy delivery, based upon input received from the power control input 65, the control circuit 161 adjusts power output to maintain an actual measured temperature at the temperature set point. The desired temperature to which the ablated tissue is exposed is set using a temperature control input 67 coupled to the control circuit 161. The actual temperature to which the ablated tissue is exposed, which is obtained from the temperature sensor 167, is reported by the temperature gauge 68, or output on display 106.

The desired duration of ablation power applied is set using the timer input 66. The clock 165 tracks the elapsed time from initial delivery of ablation power to the tissue, and counts from zero to the set point duration. The elapsed time is displayed on counter 69. The user places the treatment delivery source 166 in deliver mode by depressing the ablation power control button 62 to place the source 166 in a power "on" orientation. When in the deliver mode, the treatment delivery source 166 delivers ablation energy to the tissue in contact with the treatment element 164 until the count displayed by the clock 165 reaches the set point duration or until the power control button 62 is depressed into a power "off" orientation.

In the illustrated embodiment, the treatment delivery source 166 operates in a monopolar mode. To properly operate in this mode, an indifferent electrode 63, which is coupled to the treatment delivery source 166, is attached to the patient's back or other exterior skin area. When operated in the monopolar mode, ablating energy is emitted between the treatment element 164 and the indifferent electrode 63. Alternatively, when the treatment delivery source 166 is operated in a bipolar mode there is no indifferent electrode 63.

As previously discussed, further details on the use and structure of a suitable treatment delivery source are disclosed in U.S. Pat. No. 5,383,874 to Jackson, et al., which has been expressly and flatly incorporated herein by reference.

6. System With External Imaging

Figure 12:
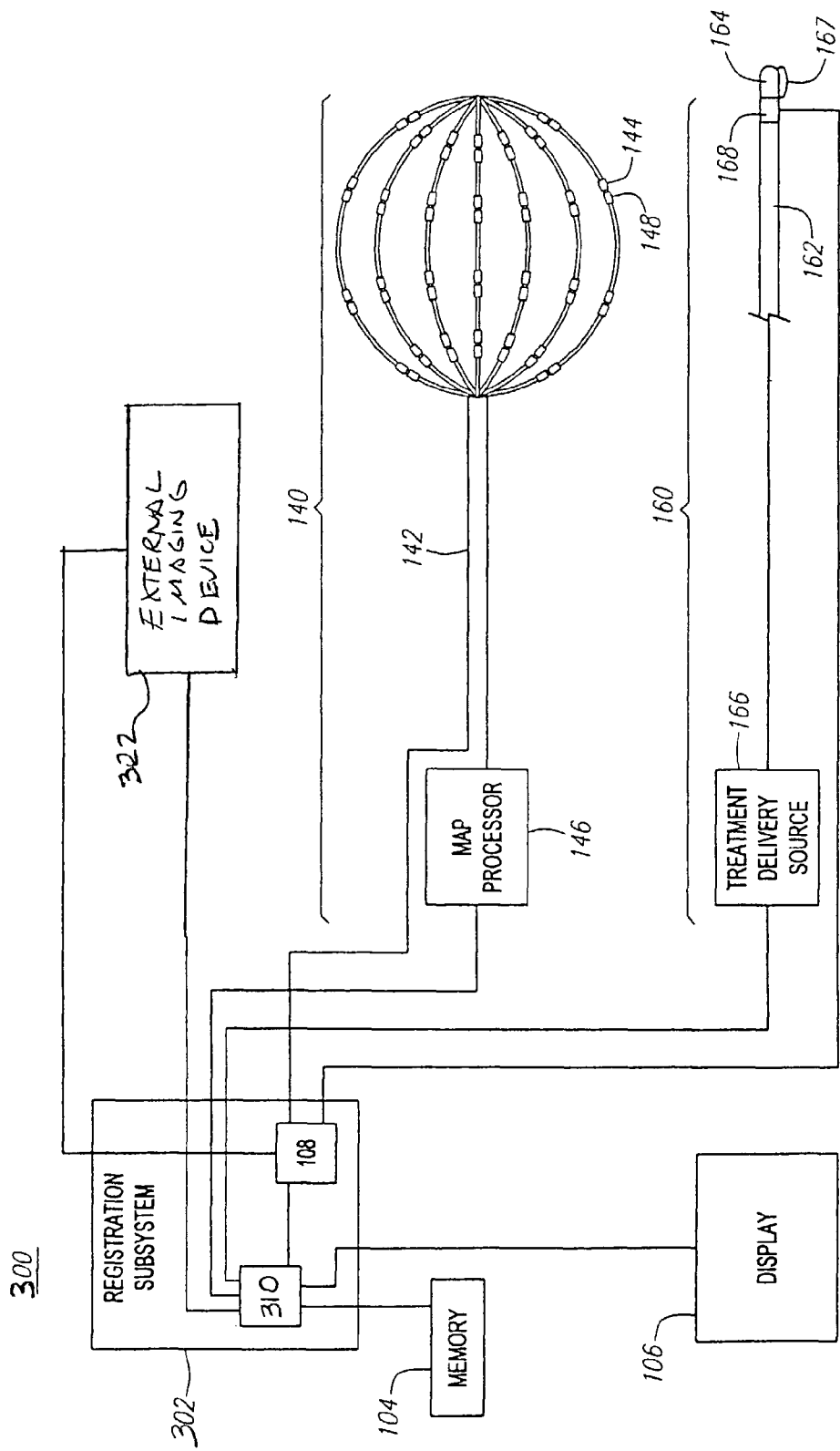
FIG. 12 is a block diagram of another preferred embodiment of a treatment system constructed in accordance with the present inventions.

Although the previously described treatment system 100 utilizes an internal imaging probe 122 in order to image the region of interest from the inside of the subject volume SV, an external imaging device can be used as well. For example, referring to FIG. 12, a treatment system 300 will now be described. The treatment system 300 is similar to the treatment system 100, with the exception that it utilizes an external imaging device 322 to provide images of the subject volume SV. As examples, the imaging device 302 can be a computerized axial tomography (CT) device or a magnetic resonance imaging (MRI) device, which can take two-dimensional image slices of the tissue, and then reconstruct these slices into a three-dimensional images of the tissue. For example, the slice images could be stored in the Diacom format and the three-dimensional renderings could be constructed using software sold by TomTec Imaging Systems, located in Germany. The imaging device 322 can be located within the operating room where the therapeutic treatment is performed, or can be remotely located, in which case, the imaging device 322 can be networked within the treatment system 300. The imaging device 322 can even generate the image off-line (e.g., a day before treatment), in which case, the image can be downloaded to the pertinent components of the treatment system 300, or can even be transferred using a suitable portable medium, such as a digital storage disk.

The treatment system 300 also comprises a registration subsystem 302 that is similar to the previously described registration subsystem 102 in that it includes a registration processor 310, which with the assistance of the location processor 108 and location elements 128 associated with the mapping elements 144 and treatment element 164, registers the mapping data acquired from the mapping subsystem 140 and the therapeutic element 164 within the three-dimensional coordinate system.

The registration subsystem 302 differs from the registration subsystem 102 in that it registers the image date acquired from the external imaging device 322 using location elements 128 that are distributed on the patient's body so that they intersect the imaging beam from the external imaging device 322. For example, if the subject volume is the heart, the location elements 128 can be suitable affixed on the chest of the patient or even within the heart itself. In this manner, the location elements 128 show up on the image as fiducial points that can be used to register the externally acquired image within the three-dimensional coordinate system. In particular, the location processor 108 determines the locations of the location elements 128 distributed on the patient's body, and then the registration processor 310 registers the three-dimensional image acquired by the external imaging device 322 by aligning the fiducial points contained in the image with the locations of the location elements 128 acquired by the location processor 108.

Alternatively, rather than distributing the location elements 128 on the patient's body to produce fiducial points on the three-dimensional image, location information of the subject volume SV can be acquired using a roving probe (e.g., the treatment device 162 or a dedicated probe) with a location element 128. In particular, the location element 128 of the roving probe can be placed in various locations within the subject volume SV, so that a number of points (e.g., 20) can be taken. Using known techniques, the registration processor 310 can then fit the three-dimensional image to the acquired points.

For example, assume that the 3-D surface obtained from the external imaging device 322 consists of a set of points $P_i(x, y, z)$:

$$SV_{322}=\{P_i(x,y,z)|i=1\ldots N\}$$

Also, assume that the user obtains a second set of points $Rj(x, y, z)$ by moving the roving probe within the subject volume:

$$SV_{rv}=\{R_j(x,y,z)|j=1\ldots M\}$$

The distance from a point Rj to the surface $SV_{322}$ can be defined as:

$$D_j=\min(dist(R_j,P_i)|i=1\ldots N)$$

In order to register the surface $SV_{322}$ in the (x, y, z) space, a series of rotations and translations can be performed to best match this surface onto the set of $R_j$ points. Preferably, the series of geometrical transformations are done such that a cost function is minimized. The following are examples of applicable cost functions:

$$C_1=1/M*\text{sum}(D_j, j=1\ldots M)$$

$$C_2=1/M*sqrt(\text{sum}(D_j^2, j=1\ldots M))$$

Other cost functions could be used. Then the transformations can be iterated using known adaptation techniques. For example, methods such as the steepest descent, gradient-based, least-squares or recursive least-squares adaptation may be employed. Such methods are described in detail in S. Haykin, *Adaptive Filter Theory*. Englewood Cliffs, N.J.: Prentice Hall, 1991.

Alternatively, the operator can even manually fit the three-dimensional image to the acquired points. In this case, at least some of the acquired points can correspond to known anatomical locations within the subject volume SV. For example, of the volume SV is a heart, the known anatomical locations can be the openings to the pulmonary veins, the right ventricular apex, the mitral valve, etc. In this manner, the operator can more efficiently and easily fit the image to the points.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of performing a procedure within a body cavity of a patient, comprising:
   introducing an imaging probe into the body cavity, wherein the imaging probe comprises an imaging element and a first location element;
   generating image data of the body cavity with the imaging element;
   introducing a mapping probe into the body cavity, wherein the mapping probe comprises one or more mapping elements and a second location element;
   generating mapping data of the body cavity with the one or more mapping elements;
   determining locations of the first location element and the second location element in a three-dimensional coordinate system;
   registering the image data and the mapping data in the coordinate system respectively based on the determined locations of the first location element and the second location element; and
   displaying the registered image data and mapping data.

2. The method of claim 1, wherein each of the first location element and the second location element comprises an orthogonal sensor array.

3. The method of claim 1, wherein each of the first location element and the second location element is wireless.

4. The method of claim 1, wherein each of the first location element and the second location element comprises an ultrasound transducer.

5. The method of claim 1, wherein the imaging element comprises an ultrasound transducer.

6. The method of claim 1, wherein the imaging element comprises an optical element.

7. The method of claim 1, wherein the one or more mapping elements comprises a plurality of mapping elements.

8. The method of claim 1, wherein the first location element is located adjacent the imaging element.

9. The method of claim 1, further comprising:
   introducing a roving probe within the body cavity, wherein the roving probe comprises a functional element and a third location element;
   determining a location of the third location element within the coordinate system;
   registering a location of the functional element in the coordinate system based on the determined location of the third location element;
   displaying the location of the functional element;
   navigating the functional element within the body cavity by reference to the display.

10. The method of claim 9, wherein the roving probe comprises a treatment probe, and the functional element comprises a treatment element, the method further comprising:
    guiding the treatment element to a target site by reference to the display; and
    treating the target site with the treatment element.

11. The method of claim 10, wherein the treatment element comprises one of the following: an ablation electrode, drug delivery needle, genetic material delivery needle, biopsy means.

12. The method of claim 1, wherein the body cavity comprises a heart chamber.

13. A method of performing a procedure within a body cavity of a patient, comprising:
    introducing an imaging probe into the body cavity, wherein the imaging probe comprises an imaging element and a first location element;
    generating image data of the body cavity with the imaging element;
    introducing a roving probe into the body cavity, wherein the roving probe comprises a functional element and a second location element;
    determining locations of the first and second elements in a three-dimensional coordinate system;
    registering the image data and the location of the functional element in the coordinate system based on the determined locations of the first and second location elements;
    displaying the registered image data and registered functional element location; and
    navigating the functional element within the body cavity by reference to the display.

14. The method of claim 13, comprising:
    introducing a mapping probe into the body cavity, wherein the mapping probe comprises one or more mapping elements and a third location element;
    generating mapping data of the body cavity with the one or more mapping elements;
    determining a location of the third location element in the coordinate system;
    registering the mapping data in the coordinate system based on the determined location of the third location element; and
    displaying registered mapping data.

15. The method of claim 14, wherein the one or more mapping elements comprises a plurality of mapping elements.

16. The method of claim 14, wherein the mapping probe is introduced into the body cavity while the imaging probe is removed from the body cavity.

17. The method of claim 14, further comprising removing the mapping probe from the body cavity, wherein the functional element is navigated within the body cavity while the mapping probe is removed from the body cavity.

18. The method of claim 13, wherein each of the first and second location elements comprises an orthogonal sensor array.

19. The method of claim 13, wherein each of the first and second location elements is wireless.

20. The method of claim 13, wherein each of the first and second location elements comprises an ultrasound transducer.

21. The method of claim 13, wherein the imaging element comprises an ultrasound transducer.

22. The method of claim 13, wherein the imaging element comprises an optical element.

23. The method of claim 13, wherein the first location element is located adjacent the imaging element, and the second location element is located adjacent the functional element.

24. The method of claim 13, wherein the roving probe is a treatment probe, the functional element is a treatment element, and the method further comprises:

guiding the treatment element to a target site by reference to the display; and treating the target site with the treatment element.

25. The method of claim 24, wherein the treatment element comprises one of the following: an ablation electrode, drug delivery needle, genetic material delivery needle, biopsy means.

26. The method of claim 13, wherein the body cavity comprises a heart chamber.

27. The method of claim 13, further comprising removing the imaging probe from the body cavity, wherein the functional element is navigated within the body cavity by reference to the display while the imaging probe is removed from the body cavity.

28. The method of claim 27, wherein the roving probe is introduced into the body cavity while the imaging probe is removed from the body cavity.

29. A system for navigating within a body cavity of a patient, comprising:
   an imaging subsystem comprising an imaging device having an imaging element, and image processing circuitry coupled to the imaging element;
   a mapping subsystem comprising a mapping device having one or more mapping, and map processing circuitry coupled to the one or more mapping elements; and
   a three-dimensional coordinate registration subsystem comprising location and registration processing circuitry and first and second location elements respectively located on the imaging device and the mapping device, the location and registration processing circuitry being coupled to the image processing circuitry, the map processing circuitry, and the first and second location elements.

30. The system of claim 29, wherein the location and registration processing circuitry comprises registration processing circuitry coupled to the image processing circuitry, and location processing circuitry coupled between the first and second location elements and the registration processing circuitry.

31. The system of claim 30, wherein the registration processing circuitry and the location processing circuitry are embodied in a single processor.

32. The system of claim 29, further comprising a treatment delivery subsystem comprising treatment device having a treatment element, and a treatment delivery source coupled to the treatment element, wherein the three-dimensional coordinate registration subsystem further comprises a third location element located on the treatment device, and the location and registration processing circuitry is further coupled to the third location element.

33. The system of claim 32, wherein the first and second location elements are respectively located adjacent the imaging element and treatment element.

34. The system of claim 32, wherein the treatment element comprises an ablation electrode, and the treatment delivery source comprises an ablation energy source.

35. The system of claim 29, wherein the location and registration processing circuitry comprises registration processing circuitry coupled to the image processing circuitry and mapping processing circuitry, and location processing circuitry coupled between the first and second location elements and the registration processing circuitry.

36. The system of claim 35, wherein the registration processing circuitry, the location processing circuitry, the image processing circuitry, and the mapping processing circuitry are embodied in a single processor.

37. The system of claim 35, wherein each of the first and second location elements comprises an orthogonal magnetic sensor array.

38. The system of claim 37, wherein the registration subsystem further comprises an antenna, a magnetic field generator coupled between the antenna and the location processing circuitry, and a magnetic field detector coupled between the orthogonal arrays of magnetic sensors and the location processing circuitry.

39. The system of claim 35, wherein each of the first and second location elements comprises an ultrasound transducer.

40. The system of claim 39, wherein the location processing circuitry comprises one or more ultrasound transducers, a first ultrasound transceiver coupled between the one or more ultrasound transducers and the location processing circuitry, and a second ultrasound transceiver coupled between the three ultrasound transducers and the location processing circuitry.

41. The system of claim 29, wherein the one or more mapping elements comprises a plurality of mapping elements.

42. The system of claim 29, further comprising a display coupled to the registration subsystem.

43. The system of claim 29, wherein the imaging element comprises an ultrasound transducer.

44. The system of claim 29, wherein the imaging device comprises an imaging catheter.

45. The system of claim 29, wherein the imaging device comprises a pullback imaging catheter.

46. The system of claim 29, wherein the imaging device comprises a real-time 3-D ultrasound catheter.

47. The system of claim 29, wherein the body cavity comprises a heart chamber.

48. A system for navigating within a body cavity of a patient, comprising:
   an imaging subsystem comprising an imaging catheter having an imaging element, and image processing circuitry coupled to the imaging element;
   a mapping subsystem comprising a mapping device having one or more mapping elements, and map processing circuitry coupled to the one or more mapping elements; and
   a three-dimensional coordinate registration subsystem comprising location and registration processing circuitry, a first location element located on the imaging device, and a second location element located on the mapping device, the location and registration processing circuitry being coupled to the image processing circuitry, the mapping processing circuitry, the first location element, and the second location element.

49. The system of claim 48, wherein the location and registration processing circuitry comprises registration processing circuitry coupled to the image processing circuitry, and location processing circuitry coupled between the first location element and the registration processing circuitry.

50. The system of claim 49, wherein the registration processing circuitry and the location processing circuitry are embodied in a single processor.

51. The system of claim 49, wherein the registration subsystem further comprises an antenna, a magnetic field generator coupled between the antenna and the location processing circuitry, and a magnetic field detector coupled between the first and second orthogonal arrays of magnetic sensors and the location processing circuitry.

52. The system of claim 48, wherein the location and registration processing circuitry comprises registration processing circuitry coupled to the image processing circuitry and mapping processing circuitry, and location processing circuitry coupled between the first and second location elements and the registration processing circuitry.

53. The system of claim 48, wherein the first location element is located adjacent the imaging element.

54. The system of claim 48, further comprising a display coupled to the registration subsystem.

55. The system of claim 48, wherein the imaging element comprises an ultrasound transducer.

56. The system of claim 48, wherein the imaging catheter comprises a pullback ultrasound catheter.

57. The system of claim 48, wherein the imaging catheter comprises a real-time 3-D imaging catheter.

58. The system of claim 48, wherein each of the first and second location elements comprises an orthogonal magnetic sensor array.

59. The system of claim 48, wherein each of the first and second location elements comprises an ultrasound transducer.

60. The system of claim 59, wherein the registration subsystem comprises one or more ultrasound transducers, a first ultrasound transceiver coupled between the one or more ultrasound transducers and the location processing circuitry, and a second ultrasound transceiver coupled between the first and second ultrasound transducers and the location processing circuitry.

61. The system of claim 48, wherein the body cavity comprises a heart chamber.

* * * * *

UNITED STATES PATENT AND TRADEMARK OFFICE
CERTIFICATE OF CORRECTION

PATENT NO.        : 8,175,680 B2
APPLICATION NO.   : 10/322695
DATED             : May 8, 2012
INVENTOR(S)       : Dorin Panescu Page 1 of 1

It is certified that error appears in the above-identified patent and that said Letters Patent is hereby corrected as shown below:

Col. 24, claim 40, line 18, remove "three"

Signed and Sealed this
Eleventh Day of September, 2012

David J. Kappos
*Director of the United States Patent and Trademark Office*